(12) United States Patent
Park et al.

(10) Patent No.: US 10,513,474 B2
(45) Date of Patent: Dec. 24, 2019

(54) CATALYST COMPOSITION AND METHOD OF PREPARING POLYOLEFIN USING THE SAME

(71) Applicant: LG CHEM, LTD., Seoul (KR)

(72) Inventors: Jin Young Park, Daejeon (KR); Yong Ho Lee, Daejeon (KR); Seung Mi Lee, Daejeon (KR); Ki Soo Lee, Daejeon (KR); Eun Ji Shin, Daejeon (KR); Seok Pil Sa, Daejeon (KR); Seul Ki Im, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 15/551,200

(22) PCT Filed: Dec. 11, 2015

(86) PCT No.: PCT/KR2015/013605
§ 371 (c)(1),
(2) Date: Aug. 15, 2017

(87) PCT Pub. No.: WO2016/186282
PCT Pub. Date: Nov. 24, 2016

(65) Prior Publication Data
US 2018/0030166 A1   Feb. 1, 2018

(30) Foreign Application Priority Data

May 15, 2015   (KR) .................. 10-2015-0068301
Dec. 10, 2015  (KR) .................. 10-2015-0175758

(51) Int. Cl.
| | | |
|---|---|---|
| C07C 2/32 | (2006.01) | |
| C08F 4/6592 | (2006.01) | |
| C08F 4/646 | (2006.01) | |
| C08F 110/02 | (2006.01) | |
| C07C 2/36 | (2006.01) | |
| C08F 110/00 | (2006.01) | |
| C08F 4/69 | (2006.01) | |
| C08F 10/00 | (2006.01) | |
| C08F 10/02 | (2006.01) | |
| B01J 21/02 | (2006.01) | |
| B01J 31/14 | (2006.01) | |
| B01J 31/16 | (2006.01) | |
| B01J 31/18 | (2006.01) | |
| B01J 31/22 | (2006.01) | |

(Continued)

(52) U.S. Cl.
CPC .............. *C07C 2/36* (2013.01); *B01J 21/02* (2013.01); *B01J 31/14* (2013.01); *B01J 31/143* (2013.01); *B01J 31/1608* (2013.01); *B01J 31/1616* (2013.01); *B01J 31/1805* (2013.01); *B01J 31/188* (2013.01); *B01J 31/2295* (2013.01); *B01J 31/24* (2013.01); *B01J 31/34* (2013.01); *C07C 2/26* (2013.01); *C07C 2/32* (2013.01); *C07C 11/02* (2013.01); *C07C 11/04* (2013.01); *C08F 4/6592* (2013.01); *C08F 4/69* (2013.01); *C08F 4/69086* (2013.01); *C08F 10/00* (2013.01); *C08F 10/02* (2013.01); *C08F 110/00* (2013.01); *B01J 21/08* (2013.01); *B01J 2231/122* (2013.01); *B01J 2231/20* (2013.01); *B01J 2531/46* (2013.01); *B01J 2531/48* (2013.01); *B01J 2531/62* (2013.01); *B01J 2540/10* (2013.01); *B01J 2540/52* (2013.01); *C07C 2521/08* (2013.01); *C07C 2523/26* (2013.01); *C07C 2531/14* (2013.01); *C07C 2531/18* (2013.01); *C07C 2531/22* (2013.01); *C07C 2531/24* (2013.01); *C07C 2531/34* (2013.01); *C08F 4/6392* (2013.01); *C08F 4/63916* (2013.01); *C08F 4/63925* (2013.01); *C08F 2410/03* (2013.01); *C08F 2420/02* (2013.01)

(58) Field of Classification Search
CPC .... C07C 2/32; C08F 4/65904; C08F 4/65927; C08F 210/02; C08F 110/02
See application file for complete search history.

(56) References Cited

U.S. PATENT DOCUMENTS

| | | | |
|---|---|---|---|
| 7,323,524 B2 * | 1/2008 | Blann ................. | B01J 31/14 526/113 |
| 8,124,557 B2 | 2/2012 | Lee et al. | |

(Continued)

FOREIGN PATENT DOCUMENTS

| | | |
|---|---|---|
| CN | 1727367 A | 2/2006 |
| CN | 101511851 A | 8/2009 |

(Continued)

OTHER PUBLICATIONS

Blann et al. "Ethylene tetramerisation: Subtle effects exhibited by N-substituted diphosphinoamine ligands" Journal of Catalysis, 2007, 249, 2, 244-249.

(Continued)

*Primary Examiner* — Caixia Lu
(74) *Attorney, Agent, or Firm* — Dentons US LLP

(57) ABSTRACT

Provided are a catalyst composition and a method of oligomerizing olefins using the same. When the catalyst composition according to the present invention is used, oligomerization and copolymerization of olefin monomers may be performed in a single reactor at the same time with high efficiency without a separate process of preparing alpha-olefin. Therefore, costs for preparing or purchasing comonomers which are expensive raw materials may be reduced, thereby reducing the production cost of a final product. Contents of SCB (short chain branch) and LCB (long chain branch) in the polyolefin may be increased without separate feeding of comonomers, thereby producing high-quality linear low-density polyethylene.

13 Claims, No Drawings

(51) Int. Cl.
  *B01J 31/24*    (2006.01)
  *B01J 31/34*    (2006.01)
  *C07C 2/26*     (2006.01)
  *C07C 11/02*    (2006.01)
  *C07C 11/04*    (2006.01)
  *B01J 21/08*    (2006.01)
  *C08F 4/639*    (2006.01)
  *C08F 4/6392*   (2006.01)

(56) References Cited

U.S. PATENT DOCUMENTS

| | | |
|---|---|---|
| 8,124,577 B2 | 2/2012 | Bernhardt et al. |
| 9,988,469 B2 * | 6/2018 | Song ............ C08F 4/64 |
| 2003/0166456 A1 | 9/2003 | Wass |
| 2005/0020788 A1 | 1/2005 | Wass |
| 2005/0228139 A1 | 10/2005 | Lee et al. |
| 2006/0128910 A1 | 6/2006 | Blann et al. |
| 2006/0173226 A1 | 8/2006 | Blann et al. |
| 2006/0211903 A1 | 9/2006 | Blann et al. |
| 2006/0229480 A1 | 10/2006 | Blann et al. |
| 2008/0027188 A1 | 1/2008 | Small et al. |
| 2010/0190939 A1 | 7/2010 | Fritz et al. |
| 2011/0172370 A1 | 7/2011 | Aliyev et al. |
| 2011/0306739 A1 | 12/2011 | Carpentier et al. |
| 2012/0101321 A1 | 4/2012 | Brown et al. |
| 2012/0123078 A1 | 5/2012 | Lee et al. |
| 2012/0172645 A1 | 7/2012 | Sydora |
| 2012/0310025 A1 | 12/2012 | Wang et al. |
| 2015/0011382 A1 | 1/2015 | Kwon et al. |
| 2015/0298110 A1 | 10/2015 | Cho et al. |
| 2015/0361118 A1 | 12/2015 | Lee et al. |
| 2016/0045906 A1 | 2/2016 | Sa et al. |
| 2016/0122571 A1 | 5/2016 | Lee et al. |
| 2016/0152742 A1 | 6/2016 | Lee et al. |
| 2016/0159828 A1 | 6/2016 | Lee et al. |
| 2016/0168281 A1 | 6/2016 | Lee et al. |
| 2016/0207946 A1 | 7/2016 | Shin et al. |
| 2016/0237187 A1 | 8/2016 | Hong et al. |
| 2016/0237188 A1 | 8/2016 | Hong et al. |
| 2016/0304637 A1 | 10/2016 | Lee et al. |
| 2017/0029346 A1 | 2/2017 | Lee et al. |
| 2018/0094085 A1 * | 4/2018 | Park ............ C08F 10/00 |
| 2018/0127333 A1 | 5/2018 | Lee et al. |

FOREIGN PATENT DOCUMENTS

| | | |
|---|---|---|
| CN | 103270006 A | 8/2013 |
| CN | 103285926 A | 9/2013 |
| CN | 103429557 A | 12/2013 |
| CN | 104245711 A | 12/2014 |
| CN | 104254547 A | 12/2014 |
| CN | 104511311 A | 4/2015 |
| EP | 2899196 A1 | 7/2015 |
| EP | 2955188 A1 | 12/2015 |
| EP | 3101039 A1 | 12/2016 |
| EP | 3243848 A1 | 11/2017 |
| JP | 2006-516265 A | 6/2006 |
| JP | 2011518034 A | 6/2011 |
| JP | 2012-526175 A | 10/2012 |
| JP | 2013515601 A | 5/2013 |
| JP | 2018508355 A | 3/2018 |
| KR | 10-2003-0017616 A | 3/2003 |
| KR | 10-2006-0002742 A | 1/2006 |
| KR | 10-2008-0074339 A | 8/2008 |
| KR | 10-2010-0045636 A | 5/2010 |
| KR | 10-1241656 B1 | 5/2010 |
| KR | 10-2011-0084303 A | 7/2011 |
| KR | 10-2012-0048468 A | 5/2012 |
| KR | 10-2013-0142151 A | 12/2013 |
| KR | 10-2014-0063346 A | 5/2014 |
| KR | 10-2014-0126613 A | 10/2014 |
| KR | 10-2015-0037581 A | 4/2015 |
| KR | 10-2015-0057988 A | 5/2015 |
| KR | 10-2015-0058049 A | 5/2015 |
| KR | 10-2005-0098663 A | 10/2015 |
| WO | 2004-076502 A1 | 9/2014 |
| WO | 2014-175495 A1 | 10/2014 |
| WO | 2015/046965 A1 | 4/2015 |
| WO | 2015/072811 A1 | 5/2015 |

OTHER PUBLICATIONS

Kuhlmann et al. "N-substituted diphosphinoamines:Toward rational ligand design for the efficient tetramerization of ethylene" Journal of Catalysis, 2007, vol. 245, pp. 279-284.

Carter et al. "High activity ethylene trimerisation catalysts based on diphosphine ligands†" Chem. Commun., 2002, 858.

Yang et al. "Novel tandem catalytic system of b-diketonate zirconium/ two different cocatalysts for preparing branched polyethylene" Catalysis communications 10 (2009) 1427-1431.

Shao et al. "Preparation and Catalytic Performance of Silica-Supported Cr(acac)3/PNP for Ethylene Tetramerization" China Petroleum Processing and Petrochemical Technology, 2014, vol. 16, No. 1, pp. 45-51.

* cited by examiner

CATALYST COMPOSITION AND METHOD OF PREPARING POLYOLEFIN USING THE SAME

CROSS-REFERENCE TO RELATED APPLICATION

This application is a National Stage Entry of International Application No. PCT/KR2015/013605 filed on Dec. 11, 2015, and claims the benefit of Korean Application No. 10-2015-0068301 filed on May 15, 2015, and Korean Application No. 10-2015-0175758 filed on Dec. 10, 2015, all of which are hereby incorporated by reference in their entirety for all purposes as if fully set forth herein.

BACKGROUND OF THE INVENTION (a) Field of the Invention

The present invention relates to a catalyst composition and a method of preparing a polyolefin using the same.

(b) Description of the Related Art

A linear alpha-olefin, which is an important material used for a comonomer, a cleaner, a lubricant, a plasticizer, etc., is commercially widely used, and particularly, 1-hexene and 1-octene are commonly used as a comonomer for controlling the density of polyethylene during preparation of linear low-density polyethylene (LLDPE).

In the existing preparation process of LLDPE (Linear Low-Density Polyethylene), copolymerization of ethylene with alpha-olefin, for example, a comonomer such as 1-hexene and 1-octene is carried out in order to control its density by forming branches in a polymer backbone.

Thus, there is a problem in that the cost of comonomers accounts for a large part of the production cost in the preparation of LLDPE having a high content of comonomers. To solve this problem, many different methods have been tried.

Further, since alpha-olefins have a different application field or market size according to the kind, a technology capable of selectively producing specific olefins is commercially very important, and recently, many studies have been carried out on a chromium catalyst technology for preparing 1-hexene or 1-octene with high selectivity through selective ethylene oligomerization.

The existing commercial preparation methods of 1-hexene or 1-octene include a SHOP process of Shell Chemical, a Ziegler process of Chevron Philips, etc., whereby C4~C20 alpha-olefins of wide distribution may be produced. However, since these methods synthesize alpha-olefins having different lengths at the same time according to a Schulz-Flory distribution, there has been a problem in that it is necessary to perform an additional separation process to obtain a specific alpha-olefin.

To solve this problem, a method of selectively synthesizing 1-hexene through trimerization of ethylene or a method of selectively synthesizing 1-octene through tetramerization of ethylene has been proposed. Further, many studies have been conducted on a catalyst system that enables selective oligomerization of ethylene.

However, although the catalyst system that enables selective oligomerization of ethylene is used, alpha-olefins produced by the oligomerization should be separated and then fed into a copolymerization process as a comonomer, together with ethylene. Thus, there are problems that the process is cumbersome and the production cost is increased.

SUMMARY OF THE INVENTION

Accordingly, an object of the present invention is to provide a catalyst composition capable of performing oligomerization and copolymerization of olefin monomers in a single reactor at the same time with high efficiency without a separate process of preparing alpha-olefin, and a method of preparing a polyolefin using the same.

According to an aspect of the present invention, provided is a catalyst composition including a first supported catalyst, in which one or more organic chromium compounds are supported on a support, and a second supported catalyst, in which one or more metallocene compounds are supported on a support, wherein the organic chromium compound includes two or more of a group represented by the following Chemical Formula 1 in a molecule, and has a linkage group (L) linking the two or more groups represented by the following Chemical Formula 1 via 4 to 8 carbon atoms, wherein the linkage group (L) is an aliphatic group having 2 to 20 carbon atoms, a heteroaliphatic group having 2 to 20 carbon atoms, an alicyclic group having 2 to 20 carbon atoms, a heteroalicyclic group having 2 to 20 carbon atoms, or a group prepared by linking two or more of the aliphatic group, the heteroaliphatic group, the alicyclic group, and the heteroalicyclic group:

[Chemical Formula 1]

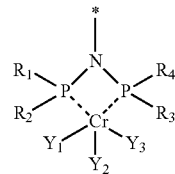

wherein * is a part which binds to the linkage group (L) linking the two or more groups, $R_1$ to $R_4$ are each independently an alkyl group having 1 to 20 carbon atoms, an alkenyl group having 2 to 20 carbon atoms, an aryl group having 6 to 20 carbon atoms, an arylalkyl group having 7 to 20 carbon atoms, an alkylaryl group having 7 to 20 carbon atoms, or an alkoxyaryl group having 7 to 20 carbon atoms;

$Y_1$, $Y_2$ and $Y_3$ are each independently halogen, hydrogen, a hydrocarbyl group having 1 to 10 carbon atoms, or a heterohydrocarbyl group having 1 to 10 carbon atoms.

Further, according to another aspect of the present invention, provided is a method of preparing a polyolefin, including the step of polymerizing olefinic monomers in the presence of the catalyst system.

When the catalyst composition according to the present invention is used, oligomerization and copolymerization of olefin monomers may be performed in a single reactor at the same time with high efficiency without a separate process of preparing alpha-olefin. Therefore, costs for preparing or purchasing comonomers which are expensive raw materials may be reduced, thereby reducing the production cost of a final product.

With regard to the catalyst composition of the present invention, alpha-olefin comonomers are primarily produced by the organic chromium compound-supported first supported catalyst, and the produced alpha-olefin comonomers remain inside the reactor, but are incorporated as comonomers for polyolefin when they are in contact with the metallocene compound-supported second supported catalyst which is a co(polymerization) catalyst, and therefore, the catalyst composition has improved copolymerization efficiency due to high accessibility to the metallocene compound and high comonomer conversion rate.

Further, since the amount of comonomers not incorporated into the polyolefin during the polymerization process is small, a fouling phenomena caused thereby may be reduced to enhance process stability, and a content of branches containing SCB (short chain branch) and LCB (long chain branch) in the polyolefin may be increased without separate feeding of comonomers, thereby producing high-quality linear low-density polyethylene.

DETAILED DESCRIPTION OF THE EMBODIMENTS

The present invention will be described in more detail in the following Examples. However, the following Examples are illustrative purposes only, and the scope of the present invention is not limited thereto.

The terminology used herein is for the purpose of describing particular embodiments only and is not intended to be limiting of the invention, unless there is a particular mention about them. The singular forms used herein are intended to include the plural forms as well, unless the context clearly indicates otherwise. It will be further understood that the term 'include', when used in this specification, specify the presence of stated features, areas, integers, steps, operations, elements, and/or components, but do not preclude the presence or addition of other features, areas, integers, steps, operations, elements, components, and/or groups.

Hereinafter, a catalyst composition and a method of preparing a polyolefin using the same according to specific embodiments of the present invention will be described in more detail.

According to an embodiment of the present invention, provided is a catalyst composition including a first supported catalyst, in which one or more organic chromium compounds are supported on a support, and a second supported catalyst, in which one or more metallocene compounds are supported on a support, wherein the organic chromium compound includes two or more of a group represented by the following Chemical Formula 1 in a molecule, and has a linkage group (L) linking the two or more groups via 4 to 8 carbon atoms, wherein the linkage group (L) is an aliphatic group having 2 to 20 carbon atoms, a heteroaliphatic group having 2 to 20 carbon atoms, an alicyclic group having 2 to 20 carbon atoms, a heteroalicyclic group having 2 to 20 carbon atoms, or a group prepared by linking two or more of the aliphatic group, the heteroaliphatic group, the alicyclic group, and the heteroalicyclic group:

[Chemical Formula 1]

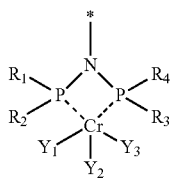

wherein * is a part which binds to the linkage group (L) linking the two or more groups, $R_1$ to $R_4$ are each independently a hydrocarbyl group or a heterohydrocarbyl group. For non-limiting example, $R_1$ to $R_4$ are each independently a substituted or unsubstituted alkyl group having 1 to 20 carbon atoms, a substituted or unsubstituted alkenyl group having 2 to 20 carbon atoms, a substituted or unsubstituted aryl group having 6 to 20 carbon atoms, a substituted or unsubstituted arylalkyl group having 7 to 20 carbon atoms, a substituted or unsubstituted alkylaryl group having 7 to 20 carbon atoms, or a substituted or unsubstituted alkoxyaryl group having 7 to 20 carbon atoms;

$Y_1$, $Y_2$ and $Y_3$ are each independently halogen, hydrogen, a hydrocarbyl group having 1 to 10 carbon atoms, or a heterohydrocarbyl group having 1 to 10 carbon atoms.

As used herein, the term 'catalyst composition' means a catalyst composition in such a state that it may be obtained as an active catalyst composition by including a first supported catalyst, in which one or more organic chromium compounds are supported on a support, and a second supported catalyst, in which one or more metallocene compounds are supported on a support separately from the first supported catalyst. The catalyst composition may be added to a reaction system in the presence or absence of any solvent and monomers, and cocatalysts which are each independently the same as or different from each other may be additionally supported on the first and second supported catalysts.

As used herein, the term 'oligomerization' means polymerization of a small number of olefinic monomers. According to the number of olefinic monomers to be oligomerized, the oligomerization is called trimerization or tetramerization, which is generally referred to as multimerization or oligomerization. Particularly, in the present invention, oligomerization means, but is not limited to, selective preparation of 1-hexene and/or 1-octene, which are main comonomers of LLDPE, from ethylene.

Selective olefin oligomerization is closely related to a catalyst system to be used. A catalyst used for olefin oligomerization includes a ligand and a transition metal coordinately binding to the ligand, in which the structure of the active catalyst may be changed according to a chemical structure of the ligand, thereby varying selectivity for alpha-olefin and activity.

The first supported catalyst included in the catalyst composition of the present invention is a supported catalyst, in which one or more organic chromium compounds are supported on a support.

According to an embodiment of the present invention, the organic chromium compound includes a previously unknown ligand compound, and it was confirmed that if a substituent introduced in the ligand compound is appropriately controlled, the electronic, steric environment around a transition metal (Cr) may be easily controlled, thereby enabling olefin oligomerization with high catalytic activity and selectivity.

The organic chromium compound according to an embodiment of the present invention includes two or more of a diphosphinoamine functional group (hereinafter, referred to as PNP) as a ligand compound, the diphosphinoamine functional groups are linked by 4 to 8 carbon atoms, and a linkage group (L) linking the diphosphinoamine functional groups may have an aliphatic group having 2 to 20 carbon atoms, a heteroaliphatic group having 2 to 20 carbon atoms, an alicyclic group having 2 to 20 carbon atoms, a heteroalicyclic group having 2 to 20 carbon atoms, or a group prepared by linking two or more of the aliphatic group, the heteroaliphatic group, the alicyclic group, and the heteroalicyclic group. Due to this structural feature, the organic chromium compound including the ligand compound may exhibit high oligomerization activity, and particularly, high selectivity for 1-hexene, 1-octene, etc., because two or more of PNP-Cr may easily interact with each other according to the electronic/steric environment around the transition metal (Cr).

Therefore, the organic chromium compound may be applied to the catalyst composition to exhibit high oligomerization activity, and particularly, high selectivity for 1-hexene, 1-octene, etc. Therefore, 1-hexene, 1-octene, etc. produced thereby is incorporated as a comonomer with high efficiency during polymerization of polyolefin, thereby preparing a high-quality polyolefin.

In the definition of Chemical Formula 1, the aryl group is preferably an aromatic ring having 6 to 20 carbon atoms, and specific examples thereof may include phenyl, naphthyl, anthracenyl, pyridyl, dimethylanilinyl, anisolyl, etc., but is not limited thereto.

The alkylaryl group means an aryl group having 6 to 20 carbon atoms, which is substituted with one or more linear or branched alkyl groups, the arylalkyl group means a linear or branched alkyl group, which is substituted with one or more aryl groups having 6 to 20 carbon atoms, and the alkoxyaryl group means an aryl group having 6 to 20 carbon atoms, which is substituted with one or more alkoxy groups.

Further, the heteroatom means N, O, F, S, or P, and the heteroaryl group means an aryl group containing one or more heteroatoms.

Further, the halogen means fluorine (F), chlorine (Cl), bromine (Br), or iodine (I).

Meanwhile, the organic chromium compound of an embodiment may include two or more of the group represented by Chemical Formula 1. A linkage group (L) linking these groups via 4 to 8 carbon atoms may be an aliphatic group having 2 to 20 carbon atoms, a heteroaliphatic group having 2 to 20 carbon atoms, an alicyclic group having 2 to 20 carbon atoms, a heteroalicyclic group having 2 to 20 carbon atoms, or a group prepared by linking two or more of the aliphatic group, the heteroaliphatic group, the alicyclic group, and the heteroalicyclic group.

Specific examples of the linkage group (L) are as follows:

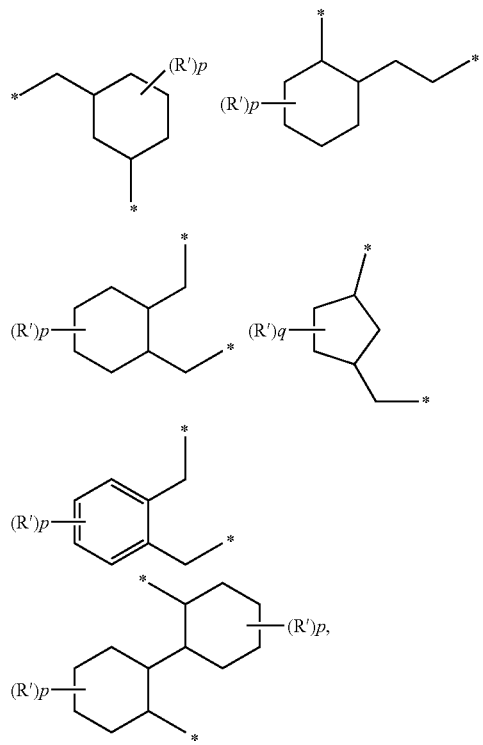

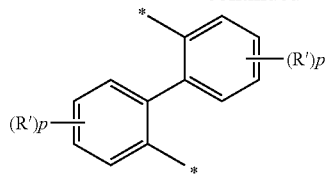

wherein * is a part which binds to N of Chemical Formula 1, R's are each independently hydrogen or alkyl having 1 to 5 carbon atoms, p is an integer of 1 to 6, q is an integer of 1 to 5, and a plurality of R's binding to one ring (cyclohexane or phenyl) are the same as or different from each other.

As such, when two or more of the group represented by Chemical Formula 1 are linked via 4 to 8 carbon atoms, the linkage group L linking the two or more of the group via 4 to 8 carbon atoms preferably includes a flexible aliphatic group in order to facilitate interactions between organic chromium complexes which are obtained by linking the two or more of the group of Chemical Formula 1.

That is, even though two or more of the group represented by Chemical Formula 1 are linked via 4 to 8 carbon atoms, if the linkage group includes only an alicyclic group or an aromatic group without the aliphatic group, for example, as the case where Chemical Formula 1 is substituted at 1- and 4-positions of cyclohexane, interactions may be extremely restricted to significantly reduce activity per unit PNP-Cr and to lower selectivity for alpha-olefins having a low carbon number such as 1-hexene and 1-octene.

The group represented by Chemical Formula 1 may be a catalyst precursor capable of progressing olefin oligomerization by coordinate binding of diphosphinoamine to chromium. As described above, the organic chromium compound of an embodiment forms a chromium complex while two or more diphosphinoamine groups are appropriately spaced, and therefore, increase of catalytic activity and improvement of selectivity due to the interaction between the two groups are confirmed in Examples described below.

According to an Example of the present invention, $R_1$ to $R_4$ of Chemical Formula 1 may be the same as each other, and preferably, phenyl.

Further, $Y_1$, $Y_2$ and $Y_3$ of Chemical Formula 1 may be each independently halogen, hydrogen, a hydrocarbyl group, or a heterohydrocarbyl group. For non-limiting example, $Y_1$, $Y_2$ and $Y_3$ may be each independently an acetylacetonate group, an acetate group, a tetrahydrofuran group, a 2-ethyl hexanonate group, a butyrate group, a pentanoate group, a laurate group, a stearate group, etc.

Meanwhile, according to an Example of the present invention, when the organic chromium compound includes two or more of the group represented by Chemical Formula 1, it may be represented by the following Chemical Formula 1-1:

[Chemical Formula 1-1]

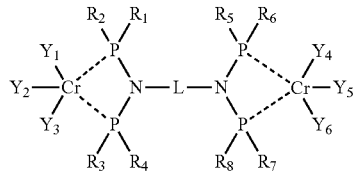

wherein L is a linkage group linking nitrogen (N) atoms via 4 to 8 carbon atoms, and is an aliphatic group having 2 to 20 carbon atoms, a heteroaliphatic group having 2 to 20 carbon atoms, an alicyclic group having 2 to 20 carbon atoms, a heteroalicyclic group having 2 to 20 carbon atoms, or a group prepared by linking two or more of the aliphatic group, the heteroaliphatic group, the alicyclic group, and the heteroalicyclic group, $R_1$ to $R_8$ are each independently an alkyl group having 1 to 20 carbon atoms, an alkenyl group having 2 to 20 carbon atoms, an aryl group having 6 to 20 carbon atoms, an arylalkyl group having 7 to 20 carbon atoms, an alkylaryl group having 7 to 20 carbon atoms, or an alkoxyaryl group having 7 to 20 carbon atoms;

$Y_1$ to $Y_6$ are each independently halogen, hydrogen, a hydrocarbyl group having 1 to 10 carbon atoms, or a heterohydrocarbyl group having 1 to 10 carbon atoms.

According to an Example of the present invention, $R_1$ to $R_8$ of Chemical Formula 1-1 may be the same as each other, and preferably phenyl. Further, specific examples of $Y_1$ to $Y_6$ of Chemical Formula 1-1 may be the same as $Y_1$, $Y_2$ and $Y_3$ described in Chemical Formula 1.

More specifically, specific examples of the organic chromium compound of Chemical Formula 1 may include the following compounds, but the present invention is not limited thereto:

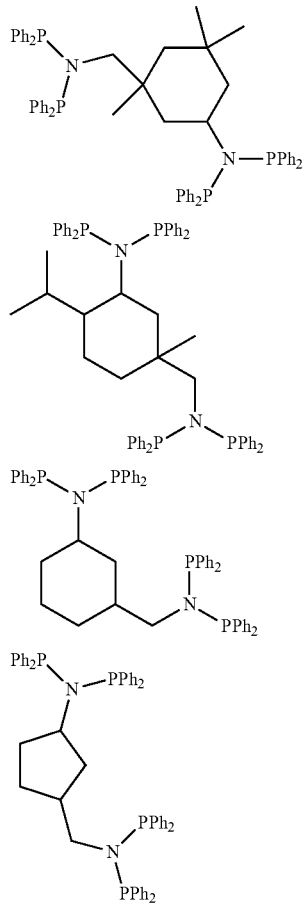

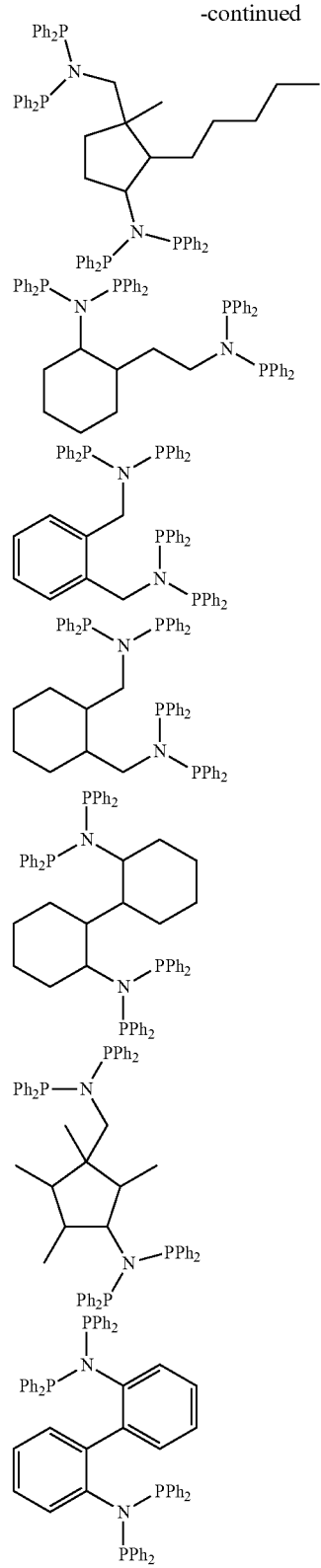

Further, specific examples of the organic chromium compound may include all possible optical isomers.

The organic chromium compound of Chemical Formula 1 is a chromium complex compound of a ligand compound of the following Chemical Formula 2, in which chromium of a chromium source forms a coordinate bond with phosphorus atoms (P) of a group represented by the following Chemical Formula 2. In the catalyst composition of the present invention, this organic chromium compound may function to induce oligomerization of olefinic monomers with excellent catalytic activity.

[Chemical Formula 2]

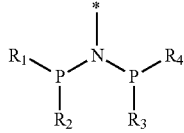

wherein * is a part which binds to the linkage group (L) linking the two or more groups, and $R_1$ to $R_4$ are each independently an alkyl group having 1 to 20 carbon atoms, an alkenyl group having 2 to 20 carbon atoms, an aryl group having 6 to 20 carbon atoms, an arylalkyl group having 7 to 20 carbon atoms, an alkylaryl group having 7 to 20 carbon atoms, or an alkoxyaryl group having 7 to 20 carbon atoms.

Specific examples of the chromium source which forms the chromium complex compound together with the ligand compound of Chemical Formula 2 may be any one or more selected from the group consisting of chromium(III)acetylacetonate, tris (tetrahydrofuran)chromium trichloride, chromium(III)-2-ethylhexanoate, chromium(III)tris(2,2,6,6-tetramethyl-3,5-heptanedionate), chromium(III)benzoylacetonate, chromium(III)hexafluoro-2,4-pentanedionate, and chromium(III)acetate hydroxide.

Meanwhile, the ligand compound of Chemical Formula 2 may be synthesized by a method such as the following Reaction Scheme 1, but the present invention is not limited thereto. A method of preparing the ligand compound represented by Chemical Formula 1-1 will be explained in more detail in Examples described below:

[Reaction Scheme 1]

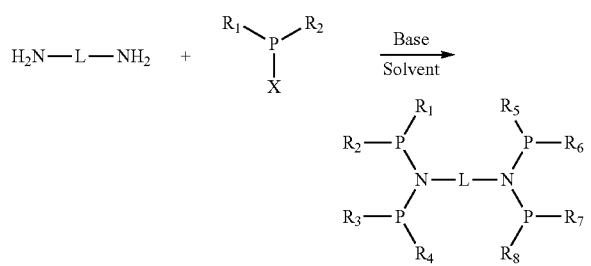

wherein definitions of $R_1$ to $R_8$ and L are the same as in the definition of Chemical Formula 1-1, and X is halogen.

The second supported catalyst included in the catalyst composition of the present invention is a supported catalyst, in which one or more metallocene compounds are supported on a support.

An alpha-olefin comonomer such as 1-hexene or 1-octene which is produced by oligomerization of olefinic monomers by the organic chromium compound supported on the first supported catalyst is copolymerized with other olefinic monomer to form a polyolefin by a catalytic action of the metallocene compound supported on the second supported catalyst in the catalyst composition of the present invention. In this regard, the alpha-olefin comonomer which is primarily produced by the organic chromium compound-supported first supported catalyst remains inside the reactor while circulating therein, but is incorporated as a comonomer for polyolefin when it is in contact with the metallocene compound-supported second supported catalyst, and due to high accessibility to the metallocene compound and high comonomer conversion rate, copolymerization efficiency is improved. Therefore, contents of SCB (short chain branch) and LCB (long chain branch) in the polyolefin may be increased without separate feeding of comonomers which are expensive raw materials, thereby producing high-quality linear low-density polyethylene.

According to an Example of the present invention, the metallocene compound may be one or more selected from compounds represented by the following Chemical Formulae 3 to 6:

$$(Cp^1R^a)_n(Cp^2R^b)M^1Z^1_{3-n}$$ [Chemical Formula 3]

wherein $M^1$ is a Group 4 transition metal;

$Cp^1$ and $Cp^2$ are the same as or different from each other, and each independently any one selected from the group consisting of cyclopentadienyl, indenyl, 4,5,6,7-tetrahydro-1-indenyl, and fluorenyl radicals, which may be substituted with hydrocarbon having 1 to 20 carbon atoms;

$R^a$ and $R^b$ are the same as or different from each other, and each independently hydrogen, C1 to C20 alkyl, C1 to C10 alkoxy, C2 to C20 alkoxyalkyl, C6 to C20 aryl, C6 to C10 aryloxy, C2 to C20 alkenyl, C7 to C40 alkylaryl, C7 to C40 arylalkyl, C8 to C40 arylalkenyl, or C2 to C10 alkynyl;

$Z^1$ is a halogen atom, C1 to C20 alkyl, C2 to C10 alkenyl, C7 to C40 alkylaryl, C7 to C40 arylalkyl, C6 to C20 aryl, substituted or unsubstituted C1 to C20 alkylidene, a substituted or unsubstituted amino group, C2 to C20 alkylalkoxy, or C7 to C40 arylalkoxy;

n is 1 or 0;

$$(Cp^3R^c)_mB^1(Cp^4R^d)M^2Z^2_{3-m}$$ [Chemical Formula 4]

wherein $M^2$ is a Group 4 transition metal;

$Cp^3$ and $Cp^4$ are the same as or different from each other, and each independently any one selected from the group consisting of cyclopentadienyl, indenyl, 4,5,6,7-tetrahydro-1-indenyl, and fluorenyl radicals, which may be substituted with hydrocarbon having 1 to 20 carbon atoms;

$R^c$ and $R^d$ are the same as or different from each other, and each independently hydrogen, C1 to C20 alkyl, C1 to C10 alkoxy, C2 to C20 alkoxyalkyl, C6 to C20 aryl, C6 to C10 aryloxy, C2 to C20 alkenyl, C7 to C40 alkylaryl, C7 to C40 arylalkyl, C8 to C40 arylalkenyl, or C2 to C10 alkynyl;

$Z^2$ is a halogen atom, C1 to C20 alkyl, C2 to C10 alkenyl, C7 to C40 alkylaryl, C7 to C40 arylalkyl, C6 to C20 aryl, substituted or unsubstituted C1 to C20 alkylidene, a substituted or unsubstituted amino group, C2 to C20 alkylalkoxy, or C7 to C40 arylalkoxy;

$B^1$ is one or more of carbon, germanium, silicon, phosphorus, or nitrogen-containing radical, or a combination thereof, which crosslinks a $Cp^3R^c$ ring with a $Cp^4R^d$ ring, or crosslinks one $Cp^4R^d$ ring to $M^2$;

m is 1 or 0;

$$(Cp^5R^e)B^2(J)M^3Z^3_2$$ [Chemical Formula 5]

wherein $M^3$ is a Group 4 transition metal;

$Cp^5$ is any one selected from the group consisting of cyclopentadienyl, indenyl, 4,5,6,7-tetrahydro-1-indenyl, and fluorenyl radicals, which may be substituted with hydrocarbon having 1 to 20 carbon atoms;

$R^e$ is hydrogen, C1 to C20 alkyl, C1 to C10 alkoxy, C2 to C20 alkoxyalkyl, C6 to C20 aryl, C6 to C10 aryloxy, C2 to C20 alkenyl, C7 to C40 alkylaryl, C7 to C40 arylalkyl, C8 to C40 arylalkenyl, or C2 to C10 alkynyl;

$Z^3$ is a halogen atom, C1 to C20 alkyl, C2 to C10 alkenyl, C7 to C40 alkylaryl, C7 to C40 arylalkyl, C6 to C20 aryl, substituted or unsubstituted C1 to C20 alkylidene, a substituted or unsubstituted amino group, C2 to C20 alkylalkoxy, or C7 to C40 arylalkoxy;

$B^2$ is one or more of carbon, germanium, silicon, phosphorus, or nitrogen-containing radical, or a combination thereof, which crosslinks a $Cp^5R^e$ ring with J; and J is any one selected from the group consisting of $NR^f$, O, $PR^f$ and S, wherein $R^f$ is C1 to C20 alkyl, aryl, substituted alkyl, or substituted aryl;

[Chemical Formula 6]

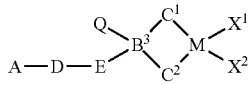

wherein A is hydrogen, halogen, a C1 to C20 alkyl group, a C2 to C20 alkenyl group, a C6 to C20 aryl group, a C7 to C20 alkylaryl group, a C7 to C20 arylalkyl group, a C1 to C20 alkoxy group, a C2 to C20 alkoxyalkyl group, a C3 to C20 heterocycloalkyl group, or a C5 to C20 heteroaryl group;

D is —O—, —S—, —N(R)— or —Si(R)(R')—, wherein R and R' are the same as or different from each other, and each independently hydrogen, halogen, a C1 to C20 alkyl group, a C2 to C20 alkenyl group, or a C6 to C20 aryl group;

E is a C1 to C10 linear or branched alkylene group;

$B^3$ is carbon, silicon, or germanium;

Q is hydrogen, halogen, a C1 to C20 alkyl group, a C2 to C20 alkenyl group, a C6 to C20 aryl group, a C7 to C20 alkylaryl group, or a C7 to C20 arylalkyl group;

M is a Group 4 transition metal;

$X^1$ and $X^2$ are the same as or different from each other, and each independently halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group;

$C^1$ and $C^2$ are the same as or different from each other, and each independently represented by any one of the following Chemical Formula 7a, Chemical Formula 7b, or Chemical Formula 7c, provided that both $C^1$ and $C^2$ are not Chemical Formula 7c;

[Chemical Formula 7a]

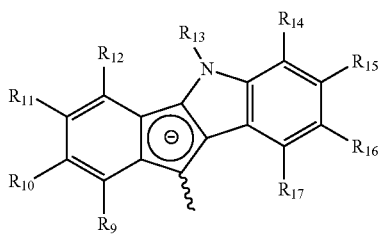

[Chemical Formula 7b]

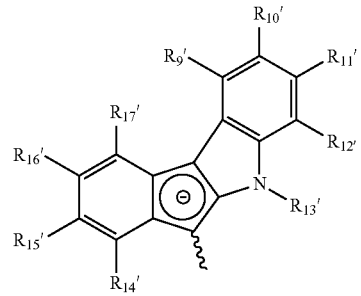

[Chemical Formula 7c]

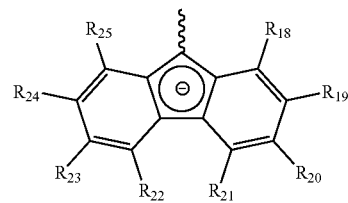

wherein R9 to R25 and R9' to R17' are the same as or different from each other, and each independently hydrogen, halogen, a C1 to C20 alkyl group, a C2 to C20 alkenyl group, a C1 to C20 alkylsilyl group, a C1 to C20 silylalkyl group, a C1 to C20 alkoxysilyl group, a C1 to C20 alkoxy group, a C6 to C20 aryl group, a C7 to C20 alkylaryl group, or a C7 to C20 arylakyl group, and two or more neighboring groups of R18 to R25 may be connected to each other to form a substituted or unsubstituted aliphatic or aromatic ring.

Meanwhile, each substituent in the metallocene compound of Chemical Formula 6 will be explained in more detail as follows.

The C1 to C20 alkyl group may include a linear or branched alkyl group, and specifically, a methyl group, an ethyl group, a propyl group, an isopropyl group, an n-butyl group, a tert-butyl group, a pentyl group, a hexyl group, a heptyl group, an octyl group, etc., but is not limited thereto.

The C2 to C20 alkenyl group may include a linear or branched alkenyl group, and specifically, an allyl group, an ethenyl group, a propenyl group, a butenyl group, a pentenyl group, etc., but is not limited thereto.

The C6 to C20 aryl group may include a monocyclic or condensed cyclic aryl group, and specifically, a phenyl group, a biphenyl group, a naphthyl group, a phenantrenyl group, a fluorenyl group, etc., but is not limited thereto.

The C5 to C20 heteroaryl group may include a monocyclic or condensed cyclic heteroaryl group, and specifically, a carbozolyl group, a pyridyl group, a quinoline group, an isoquinoline group, a thiophenyl group, a furanyl group, an imidazole group, an oxazolyl group, a thiazolyl group, a triazine group, a tetrahydropyranyl group, a tetrahydrofuranyl group, etc., but is not limited thereto.

The C1 to C20 alkoxy group may include a methoxy group, an ethoxy group, a phenyloxy group, a cyclohexyloxy group, etc., but is not limited thereto.

The Group 4 transition metal may include titanium, zirconium, hafnium, etc., but is not limited thereto.

In Chemical Formulae 7a, 7b and 7c which are ligand-derived structures included in Chemical Formula 6, R9 to R25 and R9' to R17' are preferably each independently hydrogen, a methyl group, an ethyl group, a propyl group, an isopropyl group, an n-butyl group, a tert-butyl group, a pentyl group, a hexyl group, a heptyl group, an octyl group, a phenyl group, a halogen group, a trimethylsilyl group, a triethylsilyl group, a tripropylsilyl group, a tributylsilyl group, a triisopropylsilyl group, a trimethylsilylmethyl group, a methoxy group, or an ethoxy group, but are not limited thereto.

E of the Chemical Formula 6 is more preferably a C4 to C8 linear or branched alkylene group, but is not limited thereto. Further, the alkylene group may be unsubstituted or substituted with a C1 to C20 alkyl group, a C2 to C20 alkenyl group, or a C6 to C20 aryl group.

Further, A of the Chemical Formula 6 is more preferably hydrogen, a methyl group, an ethyl group, a propyl group, an isopropyl group, an n-butyl group, a tert-butyl group, a methoxymethyl group, a tert-butoxymethyl group, a 1-ethoxyethyl group, a 1-methyl-1-methoxyethyl group, a tetrahydropyranyl group, or a tetrahydrofuranyl group, but is not limited thereto.

Further, $B^3$ of the Chemical Formula 6 is preferably silicon, but is not limited thereto.

Of the metallocene compounds, the metallocene compound represented by Chemical Formula 6 mainly contributes to making a high molecular weight copolymer having a high SCB (short chain branch) content, and the metallocene compound represented by Chemical Formula 3 mainly contributes to making a low molecular weight copolymer having a low SCB content. Further, the metallocene compound represented by Chemical Formula 4 or 5 may contribute to making a low molecular weight copolymer having a medium SCB content.

Further, according to an Example of the present invention, two or more different kinds of metallocene compounds selected from Chemical Formulae 3 to 6 are included, thereby preparing a polyolefin which has a wide molecular weight distribution to have excellent physical properties and processibility while being a high molecular weight olefin copolymer.

The metallocene compound represented by Chemical Formula 3 may be, for example, a compound represented by any one of the following structural formulae, but is not limited thereto:

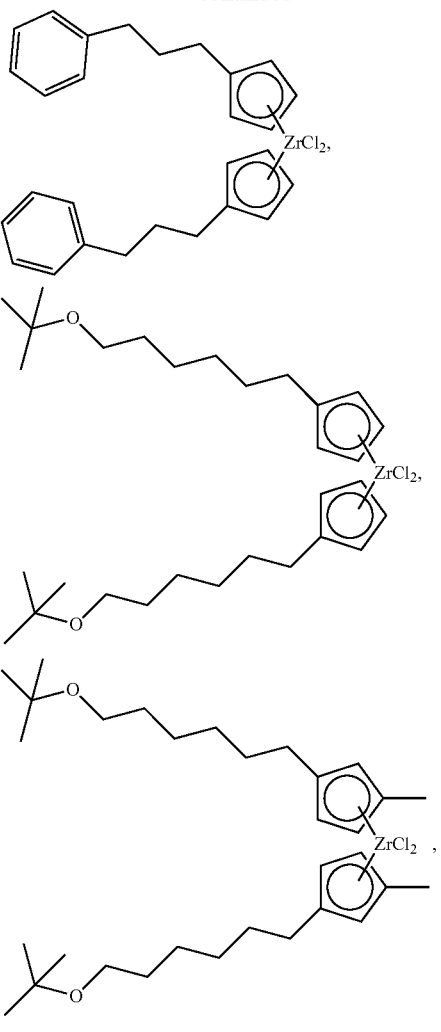

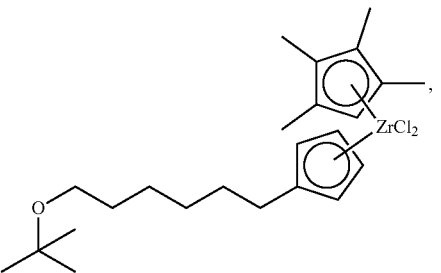

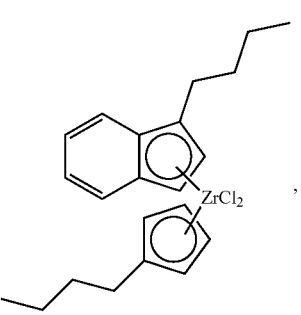

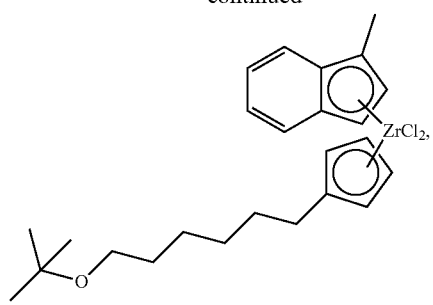
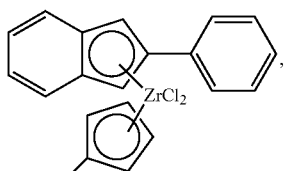
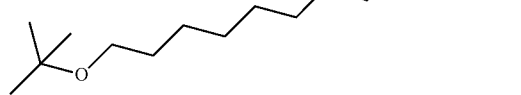
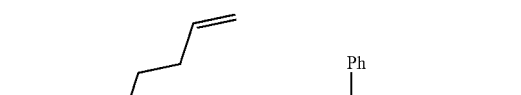
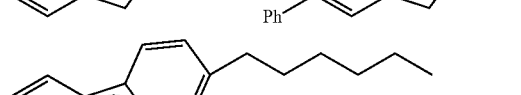
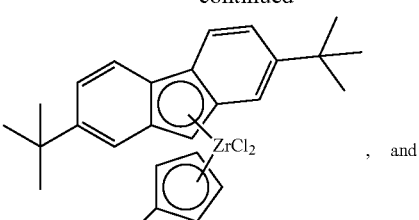
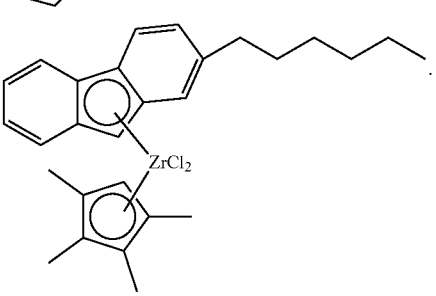
The metallocene compound represented by Chemical Formula 4 may be, for example, a compound represented by any one of the following structural formulae, but is not limited thereto:
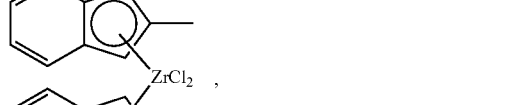
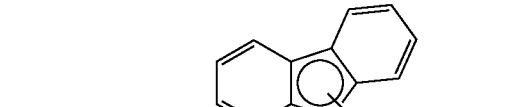
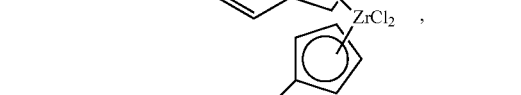
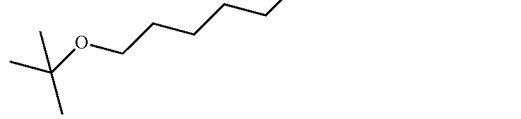

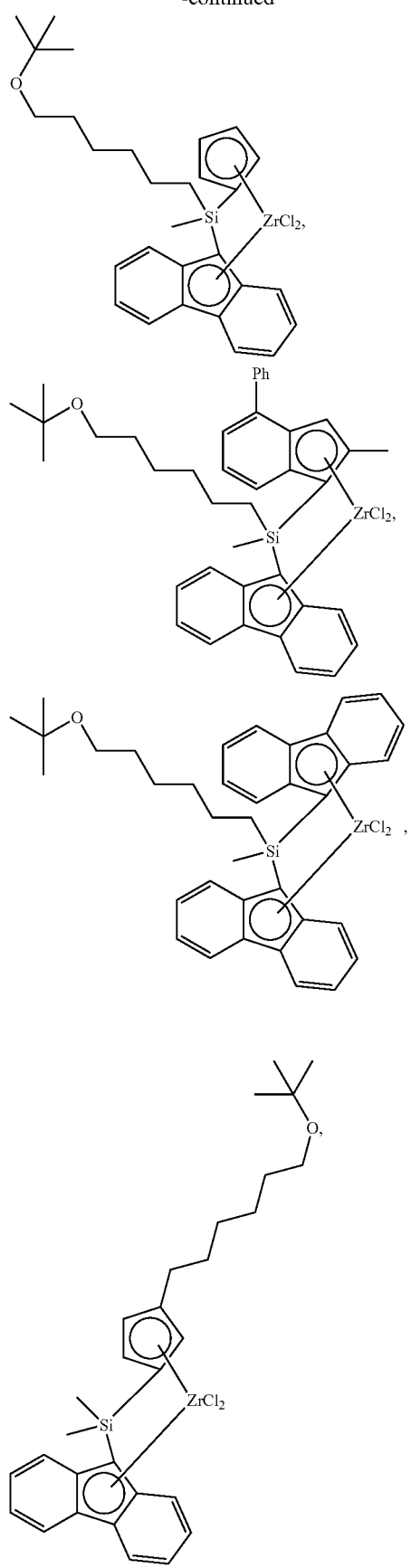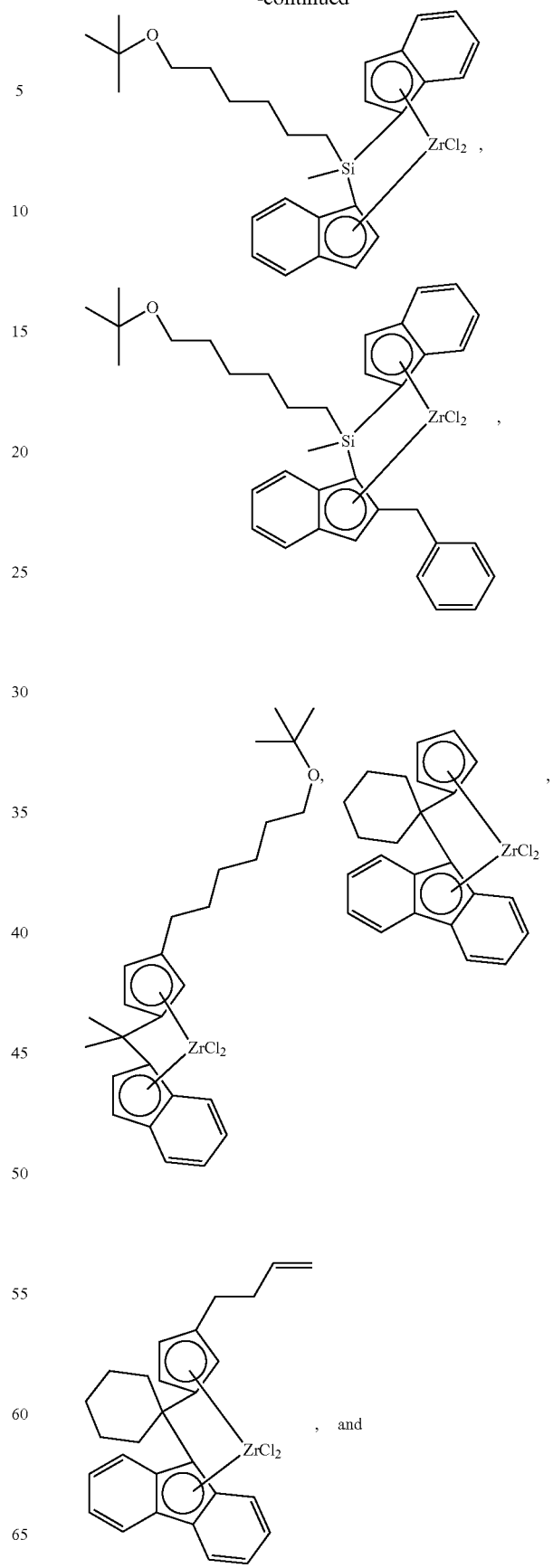

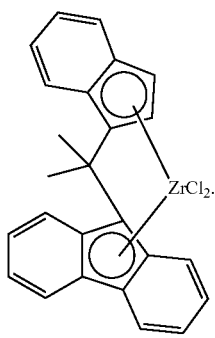
Further, the metallocene compound represented by Chemical Formula 5 may be, for example, a compound represented by any one of the following structural formulae, but is not limited thereto:
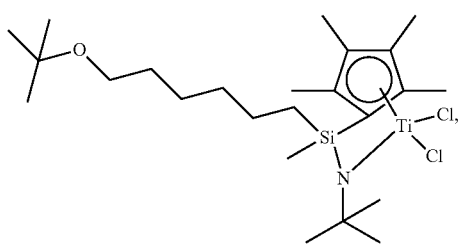
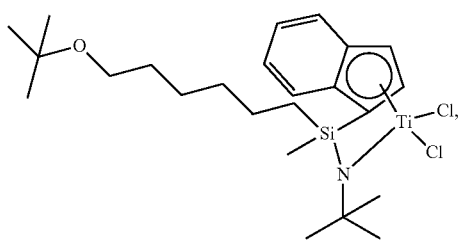
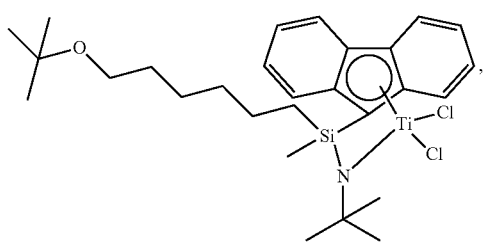
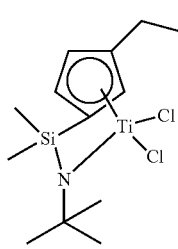
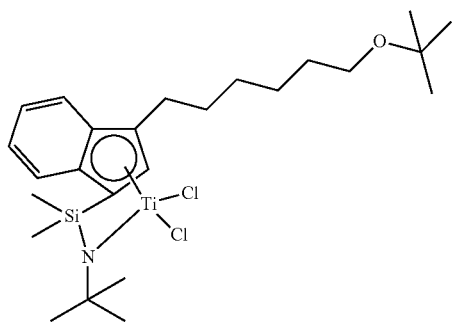
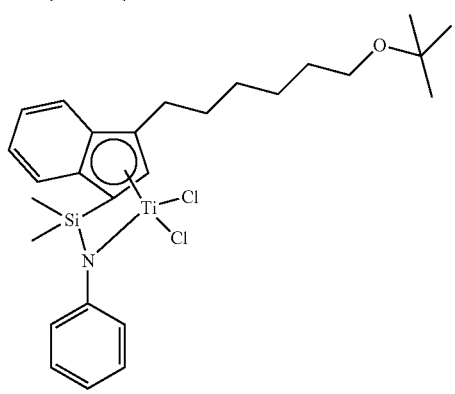
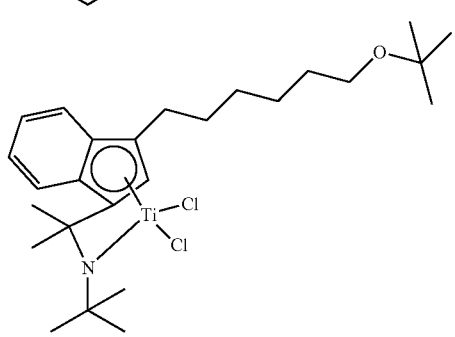
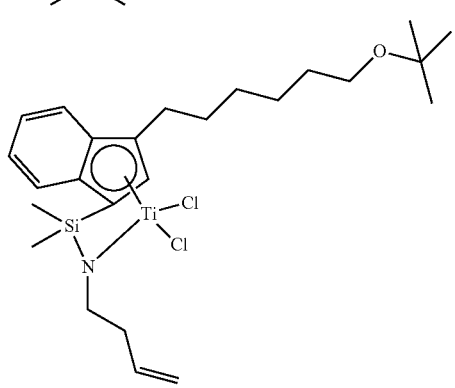
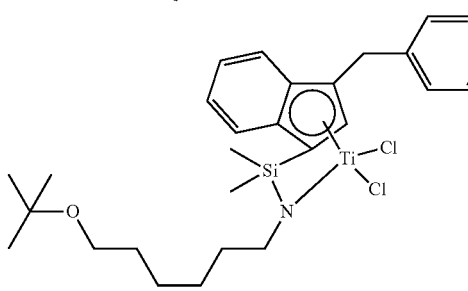, and
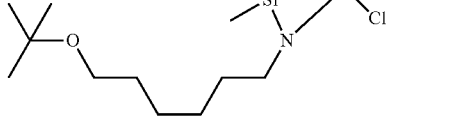

A specific example of the metallocene compound represented by Chemical Formula 6 may be a compound represented by any one of the following structural formulae, but is not limited thereto:
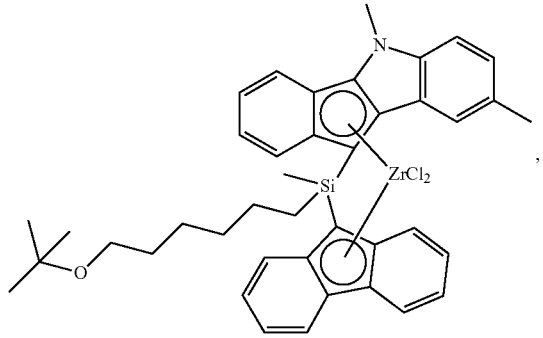
,
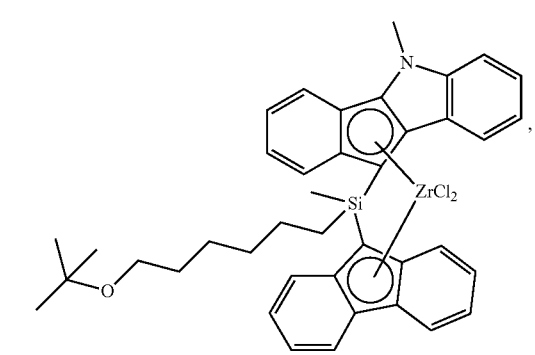
,
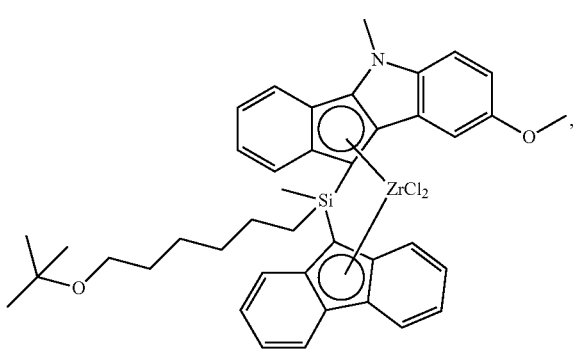
,
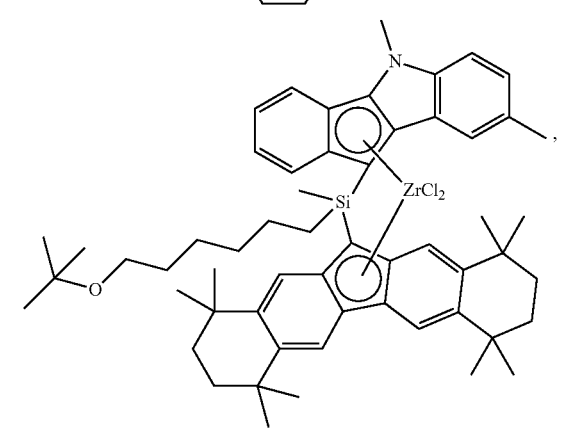
,
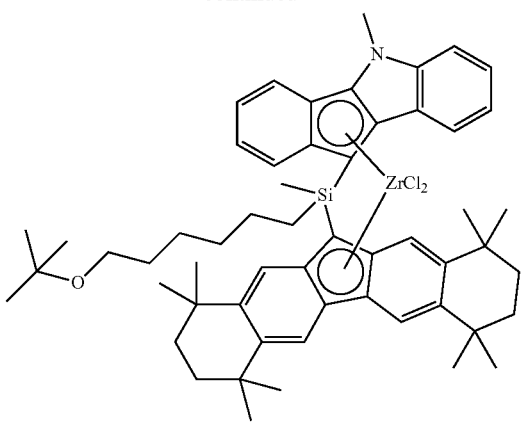
,
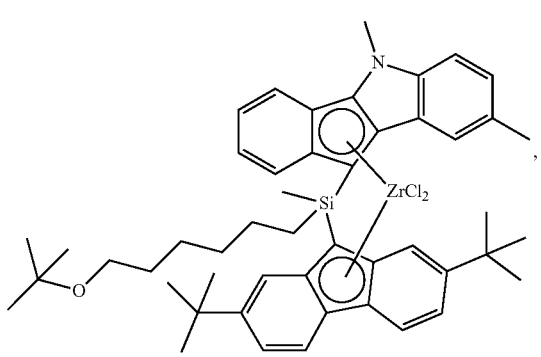
,
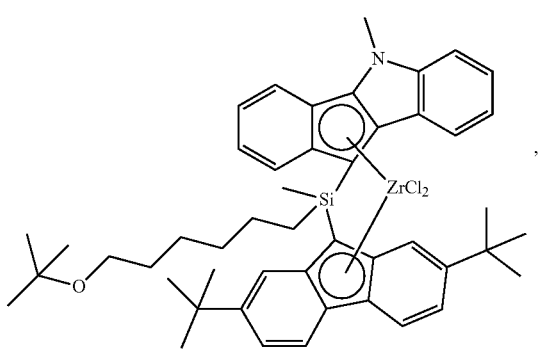
,
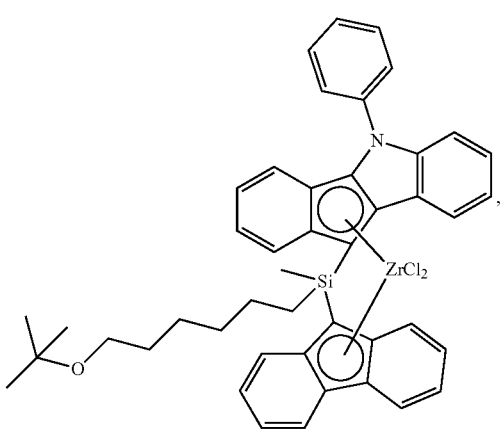
,

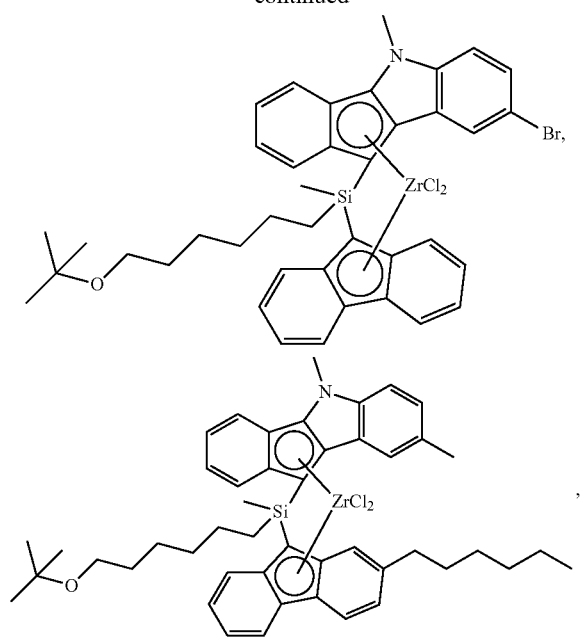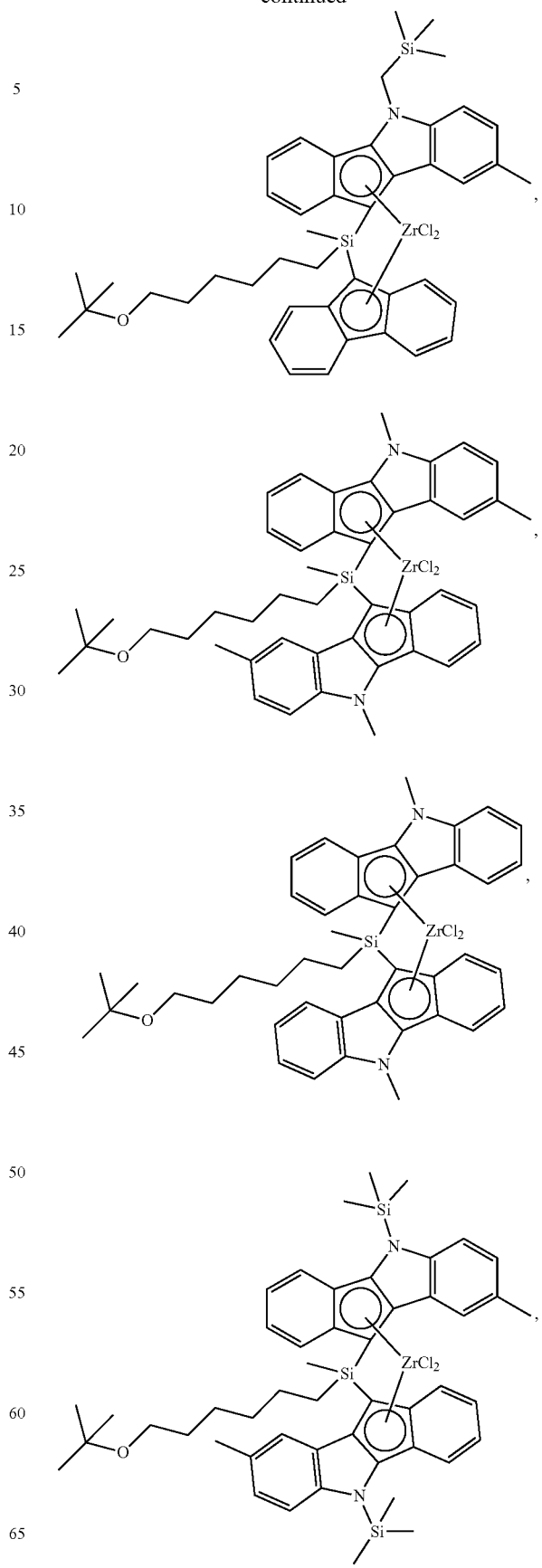

-continued

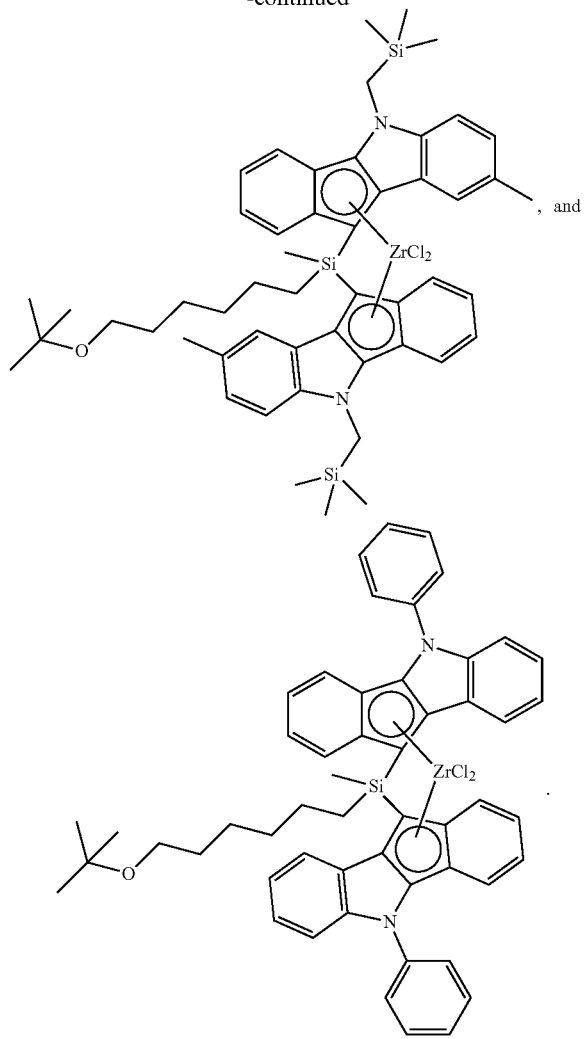, and

In the catalyst composition, one or more kinds of the above-described metallocene compounds and one or more kinds of the organic chromium compounds are separately supported on supports.

According to an Example of the invention, the first and second supported catalysts may further include each independently the same or different one or more cocatalysts of an aluminum-containing first cocatalyst of the following Chemical Formula 8 and a borate-based second cocatalyst of the following Chemical Formula 9:

—[Al($R_{26}$)—O]$k$-  [Chemical Formula 8]

wherein $R_{26}$ is the same as or different from each other, and each independently a halogen radical, a hydrocarbyl radical having 1 to 20 carbon atoms, or a hydrocarbyl radical having 1 to 20 carbon atoms, which is substituted with halogen, and k is an integer of 2 or more, $T^+[BG_4]^-$  [Chemical Formula 9]

wherein T+ is a polyatomic ion having a valence of +1, B is boron in +3 oxidation state, and Gs are each independently selected from the group consisting of a hydride group, a dialkylamido group, a halide group, an alkoxide group, an aryloxide group, a hydrocarbyl group, a halocarbyl group, and a halo-substituted hydrocarbyl group, and G has 20 or less carbon atoms, provided that G is a halide group in one or less position.

Due to the use of the first and second cocatalysts, a molecular weight distribution of the finally prepared polyolefin may become more uniform, and polymerization activity may be improved.

The first cocatalyst of Chemical Formula 8 may be an alkyaluminoxane compound including repeat units bonded in a linear, circular, or network shape, and specific examples of the first cocatalyst may include methylaluminoxane (MAO), ethylaluminoxane, isobutylaluminoxane, butylaluminoxane, etc.

Further, the second cocatalyst of Chemical Formula 9 may be a borate-based compound in the form of a tri-substituted ammonium salt, a dialkyl ammonium salt, or a tri-substituted phosphonium salt. Specific examples of the second cocatalyst may include borate-based compounds in the form of tri-substituted ammonium salts, such as trimethylammonium tetraphenylborate, methyldioctadecylammonium tetraphenylborate, triethylammonium tetraphenylborate, tripropylammonium tetraphenylborate, tri(n-butyl) ammonium tetraphenylborate, methyltetradecyclooctadecylammonium tetraphenylborate, N,N-dimethylanilinium tetraphenylborate, N,N-diethylanilinium tetraphenylborate, N,N-dimethyl(2,4,6-trimethylanilinium)tetraphenylborate, trimethylammonium tetrakis(pentafluorophenyl)borate, methylditetradecylammonium tetrakis(pentaphenyl)borate, methyldioctadecylammonium tetrakis(pentafluorophenyl) borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl(2,4,6-trimethylanilinium)tetrakis(pentafluorophenyl)borate, trimethylammonium tetrakis(2,3,4,6-tetrafluorophenyl)borate, triethylammonium tetrakis(2,3,4,6-tetrafluorophenyl)borate, tripropylammonium tetrakis(2,3,4,6-tetrafluorophenyl)borate, tri(n-butyl)ammonium tetrakis(2,3,4,6-tetrafluorophenyl)borate, dimethyl(t-butyl)ammonium tetrakis(2,3,4,6-tetrafluorophenyl)borate, N,N-dimethylanilinium tetrakis(2,3,4,6-tetrafluorophenyl)borate, N,N-diethyl anilinium tetrakis(2,3,4,6-tetrafluorophenyl)borate, N,N-dimethyl-(2,4,6-trimethylanilinium)tetrakis-(2,3,4,6-tetrafluorophenyl)borate, etc.; borate-based compounds in the form of dialkyl ammonium salts, such as dioctadecylammonium tetrakis(pentafluorophenyl)borate, ditetradecylammonium tetrakis(pentafluorophenyl)borate, dicyclohexylammonium tetrakis(pentafluorophenyl)borate, etc.; or borate-based compounds in the form of tri-substituted phosphonium salts, such as triphenylphosphonium tetrakis(pentafluorophenyl)borate, methyldioctadecylphosphonium tetrakis(pentafluorophenyl)borate, tri(2,6-dimethylphenyl) phosphonium tetrakis(pentafluorophenyl)borate, etc.

In the catalyst composition of the present invention, a molar ratio of the organic chromium compound:the metallocene compound may be about 10:1 to about 1:10, and preferably about 1:2 to about 2:1 based on the transition metal, in order to increase selectivity for linear alpha-olefin and oligomerization and copolymerization activities. However, the present invention is not limited thereto, and the molar ratio may vary depending on a polyolefin to be prepared.

In the first supported catalyst, a weight ratio of the support to the total transition metal included in the organic chromium compound may be 1:10 to 1:10,000. When the support is included in the above weight ratio, the optimum shape may be exhibited. Further, in the first supported catalyst, a weight ratio of the support to the cocatalyst compound may be 10:1 to 1:100.

In the second supported catalyst, a weight ratio of the support to the total transition metal included in the metallocene compound may be 1:10 to 1:10,000. When the support is included in the above weight ratio, the optimum shape may be exhibited. Further, in the second supported catalyst, a weight ratio of the support to the cocatalyst compound may be 10:1 to 1:100.

In the preparation method of polyolefin, the supports included in the first and second supported catalysts may be the same as or different from each other, and each independently those containing hydroxyl groups on the surface. Preferably, supports having highly reactive hydroxyl groups and siloxane groups, of which surface moisture was removed by drying, may be used.

For example, silica, silica-alumina, silica-magnesia, etc. dried at a high temperature may be used, and they may commonly contain oxide, carbonate, sulfate, and nitrate, such as $Na_2O$, $K_2CO_3$, $BaSO_4$, $Mg(NO_3)_2$, etc.

A drying temperature of the support may be preferably about 200° C. to about 800° C., more preferably about 300° C. to about 600° C., and most preferably about 300° C. to about 400° C. If the drying temperature of the support is lower than about 200° C., due to excessive moisture, surface moisture may react with the cocatalyst, and if it is higher than about 800° C., pores on the support surface may combine with each other to reduce the surface area, and a lot of hydroxyl groups may be lost on the surface and only siloxane groups may remain, thereby decreasing the reaction sites with the cocatalyst, which is not preferable.

An amount of the hydroxyl groups on the support surface may be preferably about 0.1 mmol/g to about 10 mmol/g, and more preferably about 0.5 mmol/g to about 1 mmol/g. The amount of the hydroxyl groups on the support surface may be controlled by the preparation method and conditions of the support, or drying conditions, for example, temperature, time, vacuum, spray drying, etc.

If the amount of the hydroxyl groups is less than about 0.1 mmol/g, there are fewer reaction sites with the cocatalyst, and if it is more than about 10 mmol/g, there is a possibility of being attributed to moisture other than hydroxyl groups present on the surface of support particle, which is not preferable.

The components of the first and second supported catalysts may be each independently the same as or different from each other, and added simultaneously or sequentially in a random order to a suitable solvent in the absence or presence of monomers, thereby being obtained as an active catalyst. The suitable solvent may include heptane, toluene, cyclohexane, methylcyclohexane, 1-hexene, diethylether, tetrahydrofuran, acetonitrile, dichloromethane, chloroform, chlorobenzene, methanol, acetone, etc., but is not limited thereto.

According to an Example of the present invention, the first supported catalyst may be prepared by, for example, the steps of supporting the cocatalyst compound on a support and supporting the organic chromium compound on the support. According to an Example of the present invention, the second supported catalyst may be prepared by, for example, the steps of supporting the cocatalyst compound on a support and supporting the metallocene compound on the support.

In the respective preparation methods of the first and second supported catalysts, the order of the step of supporting the organic chromium compound or the metallocene compound and the step of supporting the cocatalyst compound may be changed, if necessary. That is, the organic chromium compound or the metallocene compound is first supported on the support, and then the cocatalyst compound is additionally supported thereon to prepare the first or second supported catalyst, or the cocatalyst compound is first supported on the support, and then the organic chromium compound or the metallocene compound is additionally supported thereon to prepare the first or second supported catalyst.

Meanwhile, according to still another embodiment of the invention, provided is a method of preparing a polyolefin, including the step of polymerizing olefinic monomers in the presence of the above-described catalyst composition.

When the catalyst composition of an embodiment is used, a separate process of preparing alpha-olefin or an additional feeding of comonomers is not needed, and oligomerization and copolymerization of olefin monomers may be performed in a single reactor at the same time with high efficiency.

Ethylene may be preferably used as the olefinic monomer. The polyolefin preparation according to the present invention may be conducted using ethylene as the olefinic monomer in a single continuous slurry polymerization reactor, loop slurry reactor, gas-phase reactor, or solution reactor.

The catalyst composition may be injected into the reaction system after being dissolved or diluted in aliphatic hydrocarbon solvents having 5 to 12 carbon atoms, for example, pentane, hexane, heptanes, nonane, decane and isomers thereof, aromatic hydrocarbon solvents such as toluene and benzene, chlorine-substituted hydrocarbon solvents such as dichloromethane and chlorobenzene. It is preferable that the solvent used herein is treated with a small amount of alkyl aluminum, thereby removing a small amount of water, air, etc., which acts as a catalytic poison, and it is possible to further use a cocatalyst.

The step of polymerizing olefinic monomers may be conducted at a temperature of about 5° C. to about 200° C., and preferably, at a temperature of about 30° C. to about 150° C. Further, the step of polymerizing olefinic monomers may be conducted at a pressure of about 1 bar to about 300 bar, and preferably, at a pressure of about 2 bar to about 150 bar.

According to an Example of the present invention, polymerization may be performed by feeding olefinic monomers in the presence of hydrogen gas.

In this regard, the hydrogen gas functions to inhibit a rapid reaction of the metallocene catalyst at the initial stage of polymerization, and enables production of high molecular weight polyolefin in a larger amount. Thus, due to the use of hydrogen gas, polyolefin having a higher molecular weight and a wider molecular weight distribution may be effectively obtained.

The hydrogen gas may be fed such that a molar ratio of hydrogen gas:olefinic monomer becomes about 1:100 to about 1:1,000. If the amount of hydrogen gas used is excessively small, the sufficient catalytic activity is not achieved, and thus it is difficult to prepare a polyolefin having a desired molecular weight and molecular weight distribution. If an excessively large amount of hydrogen gas is fed, the sufficient catalytic activity is not achieved.

When the catalyst composition is reacted with olefinic monomers such as ethylene, oligomerization of olefinic monomers and polymerization of olefinic monomers occur due to contact between each of the first and second supported catalysts included in the catalyst composition and olefinic monomers. In this regard, the method of preparing the polyolefin of the present invention is not limited to sequential occurrence of the oligomerization and polymerization, and the reactions may occur simultaneously, sequentially, randomly according to contact between each of the first and second supported catalysts included in the catalyst composition and olefinic monomers.

Meanwhile, while alpha-olefins, such as propylene, 1-butene, 1-octene, 1-hexene, produced by contact between the first supported catalyst and olefinic monomers remain inside the reactor, they participate in copolymerization and are incorporated into a polyolefin when they are in contact with the second supported catalyst. Therefore, contents of SCB (short chain branch) and LCB (long chain branch) in the polyolefin may be increased without separate feeding of expensive comonomers, thereby producing high-quality linear low-density polyethylene. Further, a polyolefin of a high molecular weight is not produced by the first supported catalyst, and thus a retention time inside the reactor is prolonged while circulating for a longer time. Therefore, it is possible to continuously produce and feed alpha-olefin comonomers during polyolefin polymerization.

Hereinafter, the present invention will be explained in detail with reference to Examples of the present invention. However, it must be interpreted in such a way that these examples may be modified in various forms and the scope of the invention is not limited thereto.

SYNTHESIS OF COMPOUND

All reactions were progressed using Schlenk technique or a Glove box under argon atmosphere. The synthesized compounds were analyzed by $^1$H (500 MHz) and $^{31}$P (202 MHz) NMR spectra using a Varian 500 MHz spectrometer. Shift was expressed in ppm, downfield from TMS, with a residual solvent peak as a reference. A phosphorous probe was calibrated with aqueous $H_3PO_4$.

Synthesis Example of Organic Chromium Compound

Synthesis Example 1

1-1> Synthesis of Ligand Compound

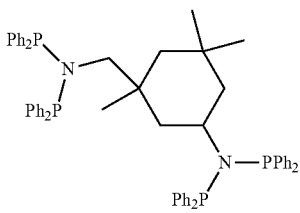

Under argon atmosphere, 3-(aminomethyl)-3,5,5-trimethylcyclohexanamine (5 mmol) and triethylamine (3~10 equiv. to amine) were dissolved in dichloromethane (80 mL). While flak was immersed in a water bath, chlorodiphenylphosphine (20 mmol, 4 equiv. to amine) was slowly introduced, followed by agitation overnight. The solvent was removed under vacuum, and then THF was introduced. This mixture was sufficiently agitated, and a triethylammonium chloride salt was removed with an air-free glass filter. The solvent was removed from the filtrate to obtain a product.

$^{31}$P NMR (202 MHz, $CDCl_3$): 45.6 (br s), 56.2 (br s)

1-2> Synthesis of Organic Chromium Compound

Under argon gas, chromium(III) acetylacetonate(Cr(acac)$_3$) (244.5 mg, 0.7 mmol) and the ligand compound (0.5 equiv. to chromium(Cr)) prepared in the Synthesis Example 1 were put in a flask. 65 mL of toluene was added to prepare 11 mM of an organic chromium compound solution (based on Cr).

Synthesis Example of Metallocene Compound

Synthesis Example 2: (tBu-O—(CH$_2$)$_6$—C$_5$H$_4$)$_2$ZrCl$_2$ t-Butyl-O—(CH$_2$)$_6$—Cl was prepared using 6-chlorohexanol according to a method suggested in a literature (Tetrahedron Lett. 2951 (1988)), and reacted with NaCp to prepare t-Butyl-O—(CH$_2$)$_6$—C$_5$H$_5$ (yield 60%, b.p. 80° C./0.1 mmHg).

Further, t-Butyl-O—(CH$_2$)$_6$—C$_5$H$_5$ was dissolved in THF at −78° C., and normal butyl lithium (n-BuLi) was slowly added thereto. The temperature was raised to room temperature, and the mixture was allowed to react for 8 hours. A solution of the synthesized lithium salt was slowly added to a suspension solution of ZrCl$_4$(THF)$_2$ (1.70 g, 4.50 mmol)/THF (30 mL) at −78° C., and allowed to react at room temperature for 6 hours.

All the volatile materials were removed under vacuum, and a hexane solvent was added to the obtained oily liquid material, followed by filtration. The filtered solution was dried under vacuum, and hexane was added thereto to induce precipitation at a low temperature (−20° C.). The resultant precipitate was filtered at a low temperature to obtain a [tBu-O—(CH$_2$)$_6$—C$_5$H$_4$]$_2$ZrCl$_2$ compound as a white solid (yield 92%).

$^1$H NMR (300 MHz, CDCl$_3$): 6.28 (t, J=2.6 Hz, 2 H), 6.19 (t, J=2.6 Hz, 2 H), 3.31 (t, 6.6 Hz, 2 H), 2.62 (t, J=8 Hz), 1.7-1.3 (m, 8 H), 1.17 (s, 9 H).

$^{13}$C NMR (CDCl$_3$): 135.09, 116.66, 112.28, 72.42, 61.52, 30.66, 30.61, 30.14, 29.18, 27.58, 26.00.

Synthesis Example 3: (tBu-O—(CH$_2$)$_6$)(CH$_3$)Si(C$_5$(CH$_3$)$_4$)(tBu-N)TiCl$_2$ 50 g of Mg(s) was added to a 10 L reactor at room temperature, and 300 mL of THF was added thereto. About 0.5 g of I$_2$ was added thereto, and the reactor temperature was maintained at 50° C. After the reactor temperature was stabilized, 250 g of 6-t-buthoxyhexyl chloride was added to the reactor at a speed of 5 mL/min by using a feeding pump. According to the addition of 6-t-buthoxyhexyl chloride, it was observed that the reactor temperature was increased by about 4° C. to about 5° C. While 6-t-buthoxyhexyl chloride was continuously added, agitation was performed for 12 hours. A black reaction solution was obtained after reaction for 12 hours. After 2 mL of the produced black solution was sampled, water was added thereto to obtain an organic layer. Thus, 6-t-buthoxyhexane was confirmed by 1H-NMR. 6-t-buthoxyhexane indicated that the Grignard reaction was well performed. Accordingly, 6-t-buthoxyhexyl magnesium chloride was synthesized.

After 500 g of MeSiCl$_3$ and 1 L of THF were added to the reactor, the reactor temperature was cooled to −20° C. 560 g of the synthesized 6-t-buthoxyhexyl magnesium chloride was added to the reactor by using a feeding pump at a speed of 5 mL/min After feeding of the Grignard reagent was finished, the reactor temperature was slowly increased to room temperature and agitation was performed for 12 hours. After reaction for 12 hours, it was confirmed that the white MgCl$_2$ salt was generated. 4 L of hexane was added and the salt was removed through labdori to obtain a filter solution. After the resulting filter solution was added to the reactor, hexane was removed at 70° C. to obtain a light yellow liquid. It was confirmed by 1H-NMR that the obtained liquid was a desired methyl(6-t-buthoxy hexyl)dichlorosilane} compound.

$^1$H-NMR (CDCl$_3$): 3.3 (t, 2H), 1.5 (m, 3H), 1.3 (m, 5H), 1.2 (s, 9H), 1.1 (m, 2H), 0.7 (s, 3H)

After 1.2 mol (150 g) of tetramethylcyclopentadiene and 2.4 L of THF were added to the reactor, the reactor temperature was cooled to −20° C. 480 mL of n-BuLi was added to the reactor by using the feeding pump at a speed of 5 mL/min After n-BuLi was added, the reactor temperature was slowly increased to room temperature and agitation was performed for 12 hours. After reaction for 12 hours, an equivalent of methyl(6-t-buthoxy hexyl)dichlorosilane (326 g, 350 mL) was rapidly added to the reactor. The reactor temperature was slowly increased to room temperature and agitation was performed for 12 hours. Then, the reactor temperature was cooled to 0° C., and 2 equivalents of t-BuNH$_2$ was added. The reactor temperature was slowly increased to room temperature and agitation was performed for 12 hours. After reaction for 12 hours, THF was removed, and 4 L of hexane was added to obtain a filter solution, from which the salt was removed by using the labdori. After the filter solution was added to the reactor, hexane was removed at 70° C. to obtain a yellow solution. It was confirmed by 1H-NMR that the obtained yellow solution was a methyl(6-t-buthoxyhexyl)(tetramethylCpH)t-butylaminosilane compound.

TiCl$_3$(THF)$_3$ (10 mmol) was rapidly added to n-BuLi and the dilithium salt of the ligand at −78° C., which was synthesized from the ligand dimethyl(tetramethylCpH)t-butylaminosilane in the THF solution. The reaction solution was agitated for 12 hours while the temperature was slowly increased from −78° C. to room temperature. After agitation was performed for 12 hours, an equivalent of PbCl$_2$ (10 mmol) was added to the reaction solution at room temperature and agitation was performed for 12 hours. After agitation was performed for 12 hours, a dark black solution having the blue color was obtained. After THF was removed from the resulting reaction solution, hexane was added to filter the product. After hexane was removed from the filter solution, it was confirmed by 1H-NMR that the solution was (tBu-O—(CH$_2$)$_6$)(CH$_3$)Si(C$_5$(CH$_3$)$_4$)(tBu-N)TiCl$_2$ which is a desired [methyl(6-t-buthoxyhexyl)silyl(η5-tetramethylCp)(t-Butylamido)]TiCl$_2$).

1H-NMR (CDCl$_3$): 3.3 (s, 4H), 2.2 (s, 6H), 2.1 (s, 6H), 1.8~0.8 (m), 1.4 (s, 9H), 1.2 (s, 9H), 0.7 (s, 3H)

Preparation Example of First Supported Catalyst

Preparation Example 1

Silica was dehydrated and dried under vacuum at 200° C. for 10 hours.

7 g of the prepared silica support was added to a glass reactor at 40° C., and a methylaluminoxane (MAO) solution in which 70 mmol of aluminum was contained in a toluene solution was added thereto and supported.

Next, a toluene solution of the organic chromium compound prepared in Synthesis Example 1 was added to the glass reactor and allowed to react under agitation for 2 hours. Agitation was stopped and a filtrate was removed. The resulting product was washed with a sufficient amount of toluene and further washed with 100 mL of hexane. 3.1 mL of 2 wt % antistatic agent was added, followed by agitation. Then, a slurry solution was transferred to a flask replaced by argon, and then a filtrate was removed, and drying under vacuum was performed to obtain a first supported catalyst in the form of solid powder.

Preparation Example of Second Supported Catalyst

Preparation Example 2

Silica (manufactured by Grace Davison, Co., Ltd., SP952) was dehydrated and dried under a vacuum at 200° C. for 10 hours.

10 g of the prepared silica support was added to a glass reactor at 40° C., and 91 mL of 10 wt % methylaluminoxane (MAO) in a toluene solution was added thereto, followed by supporting under agitation for 12 hours or longer.

Next, 100 mL of toluene was added, and then 0.0689 mmol/g of the metallocene compound prepared in Synthesis Example 3 was added and agitated for 1 hour. Next, 0.618 mmol/g of the metallocene compound prepared in Synthesis Example 2 was added and allowed to react for 1 hour.

After reaction, agitation was stopped and a toluene layer was separated and removed. The toluene was removed under reduced pressure to obtain a second supported catalyst.

Example of Polyolefin Polymerization

Example 1

Oligomerization was performed in a 600 mL temperature-controllable metal alloy reactor for high pressure, equipped with a mechanical stirrer.

19 mg of the first supported catalyst prepared in Preparation Example 1 and 6.6 mg of the second supported catalyst prepared in Preparation Example 2 were weighed in a dry box and put in a 50 mL glass bottle. The bottle was sealed with a rubber diaphragm and taken out of the dry box, and a supported catalyst to be injected into the reactor was prepared.

400 mL of hexane and the prepared supported catalyst were added to the reactor without contact with air. Reaction was allowed for 1 hour while continuously applying a gaseous ethylene monomer at a pressure of 30 bar. The reaction was terminated by stopping agitation and then by exhausting ethylene.

Thereafter, 2~3 mL of the liquid part of the reactor was taken and quenched with water, and an organic layer was filtered with a PTFE syringe filter to perform GC analysis. The remaining solution was filtered to obtain a polymer, and this polymer was dried in a vacuum oven at 60° C. for 12 hours or longer, followed by weighing. Further, a content of branches in the polyolefin was analyzed by NMR analysis of the dried polymer.

Comparative Example 1

Polyolefin polymerization was performed in the same manner as in Example 1, except that 6.6 mg of the second supported catalyst was only used as the catalyst composition without using the first supported catalyst in Example 1.

Comparative Example 2

Polyolefin polymerization was performed in the same manner as in Comparative Example 1, except that 9.5 mg of the second supported catalyst was only used as the catalyst composition and 20 mL of 1-hexene as a comonomer was injected into the reactor in Comparative Example 1.

Polymerization activity in Examples and Comparative Examples and physical properties of the resulting polyolefins are shown in the following Table 1.

TABLE 1

| Example No. | Activity (kgPE/ gSiO$_2$/hr) | Physical properties of polyolefin | | Alpha-olefin remaining after polymerization | |
|---|---|---|---|---|---|
| | | Mw (g/mol) | Branch terminal (mol %) | 1-Hx(g) | 1-Oc(g) |
| Example 1 | 12.0 | 312,000 | 0.5 (C4 or more branch) | 2.5 | 1.3 |
| Comparative Example 1 | 13.1 | 560,000 | none | 0 | 0 |
| Comparative Example 2 | 7.4 | 368,000 | 0.5 (C4 branch) | 13.0 | 0 |

In the polyolefin of Example 1, a content of the copolymers was confirmed by normalizing an integral value of the main chain in 1H NMR spectrum to 1000, and then calculating a molar ratio of branches of each sample. In more detail, when an analytical value of a different terminal structure is obtained from the copolymerized polyolefin, the remainder excluding terminal structures having double bonds (that is, alpha-olefins which did not participate in the copolymerization) was assumed as the copolymerized polyolefin, and the main chain was taken as 1000 to calculate a relative terminal ratio. In this regard, it was assumed that the terminal structures having double bonds have the same molecular weight and are produced at the same molar ratio.

Referring to Table 1, in Comparative Example 1, ethylene was copolymerized without comonomers by using only the metallocene compound-supported catalyst, and as a result, no copolymer chains were found.

In Comparative Example 2, polymerization was performed by using only the metallocene compound-supported catalyst and introducing 1-hexene as a comonomer, and as a result, it was confirmed that a polyolefin copolymerized with 1-hexene was produced. Meanwhile, in Comparative Example 2, 20 mL of 1-hexene was introduced, but about 13 g (19.3 mL) of 1-hexene was found in a solution remaining after synthesis, indicating that a significant amount of 1-hexene was not incorporated during copolymerization and remained.

In contrast, in Example 1, copolymerization was performed with only ethylene by using the organic chromium compound-supported first supported catalyst and the metallocene compound-supported second supported catalyst, and as a result, it was confirmed that C4 or more branches were copolymerized at the terminal of polyolefin at a molar ratio similar to that of Comparative Example 2, although comonomers were not used. Therefore, it can be seen that ethylene was oligomerized by the first supported catalyst to produce alpha-olefin comonomers such as 1-hexene, and the produced comonomers were successfully incorporated during copolymerization.

Additionally, presence of 2.5 g of 1-hexene and 1.3 g of 1-octene in a solution remaining after synthesis in Example 1 was confirmed by GC analysis, and various comonomers such as 1-octene as well as 1-hexene were found. In particular, the amount of alpha-olefins incorporated into the polyolefin of Example 1 was similar to that of Comparative Example 2, but the amount of alpha-olefins remaining after polymerization was smaller than that of Comparative Example 2, suggesting that the similar level of comonomer incorporation occurred even at a low concentration of comonomers in the reaction system. Accordingly, it can be seen that the catalyst system of the present invention exhibits a high comonomer incorporation rate.

What is claimed is:

1. A catalyst composition, comprising;
a first supported catalyst having one or more organic chromium compounds supported on a support; and
a second supported catalyst having one or more metallocene compounds supported on a support,
wherein the organic chromium compound includes two or more of a group represented by the following Chemical Formula 1 in a molecule, and has a linkage group (L) linking the two or more groups represented by the following Chemical Formula 1 via 4 to 8 carbon atoms in the linkage group (L):

[Chemical Formula 1]

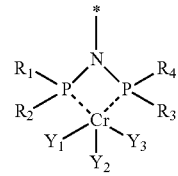

wherein * is a part which binds to the linkage group (L) linking the two or more groups,
$R_1$ to $R_4$ are each independently an alkyl group having 1 to 20 carbon atoms, an alkenyl group having 2 to 20 carbon atoms, an aryl group having 6 to 20 carbon atoms, an arylalkyl group having 7 to 20 carbon atoms, an alkylaryl group having 7 to 20 carbon atoms, or an alkoxyaryl group having 7 to 20 carbon atoms;
$Y_1$, $Y_2$ and $Y_3$ are each independently halogen, hydrogen, a hydrocarbyl group having 1 to 10 carbon atoms, or a heterohydrocarbyl group having 1 to 10 carbon atoms, and
wherein the linkage group (L) is a group selected from the group consisting of the following Chemical Formulae:

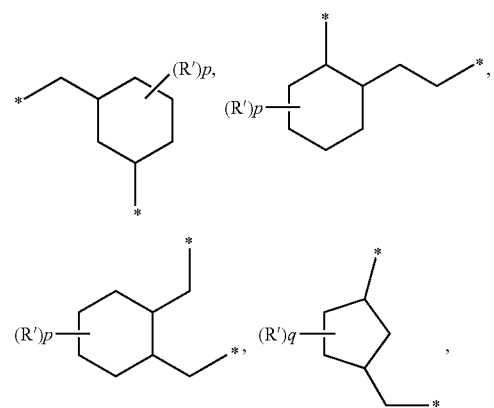

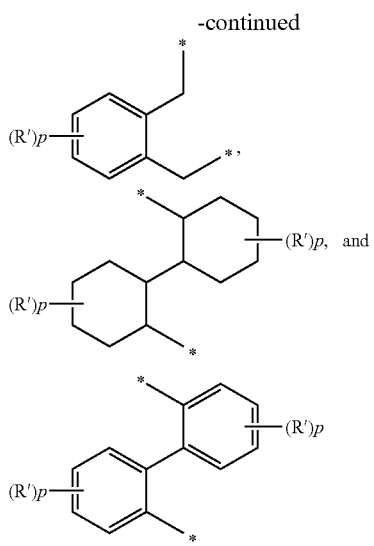

wherein * is a part which binds to N of Chemical Formula 1,

R's are each independently hydrogen or alkyl having 1 to 5 carbon atoms, p is an integer of 1 to 6, q is an integer of 1 to 5, and a plurality of R's binding to one ring are the same as or different from each other.

2. The catalyst composition of claim 1, wherein the organic chromium compound is represented by the following Chemical Formula 2:

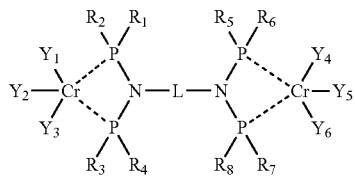

[Chemical Formula 2]

wherein L is a linkage group linking nitrogen (N) atoms via 4 to 8 carbon atoms in the linkage group, and is an aliphatic group having 2 to 20 carbon atoms, a heteroaliphatic group having 2 to 20 carbon atoms, an alicyclic group having 2 to 20 carbon atoms, a heteroalicyclic group having 2 to 20 carbon atoms, or a group of two or more of the aliphatic group, the heteroaliphatic group, the alicyclic group, and the heteroalicyclic group, which are linked together, $R_1$ to $R_8$ are each independently an alkyl group having 1 to 20 carbon atoms, an alkenyl group having 2 to 20 carbon atoms, an aryl group having 6 to 20 carbon atoms, an arylalkyl group having 7 to 20 carbon atoms, an alkylaryl group having 7 to 20 carbon atoms, or an alkoxyaryl group having 7 to 20 carbon atoms; and $Y_1$ to $Y_6$ are each independently halogen, hydrogen, a hydrocarbyl group having 1 to 10 carbon atoms, or a heterohydrocarbyl group having 1 to 10 carbon atoms.

3. The catalyst composition of claim 1, wherein $R_1$ to $R_4$ of the Chemical Formula 1 are phenyl.

4. The catalyst composition of claim 1, wherein the organic chromium compound is selected from the group consisting of the following Chemical Formulae:

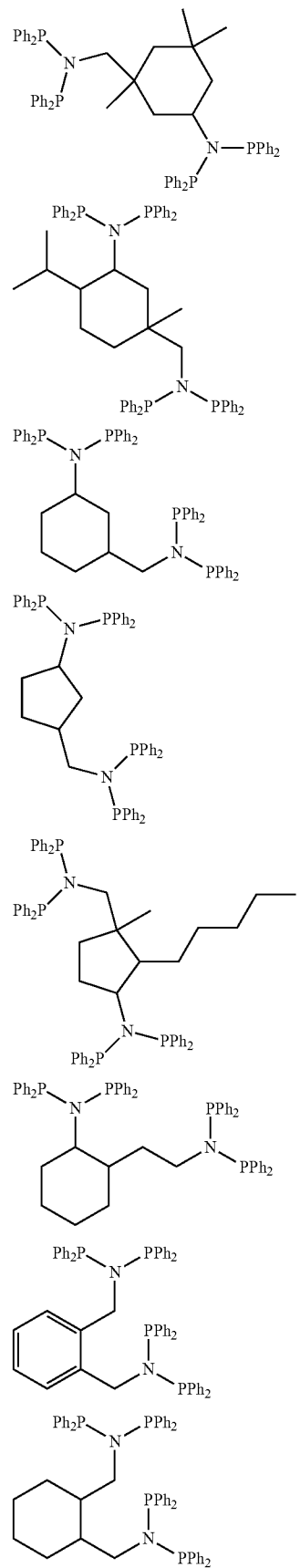

-continued

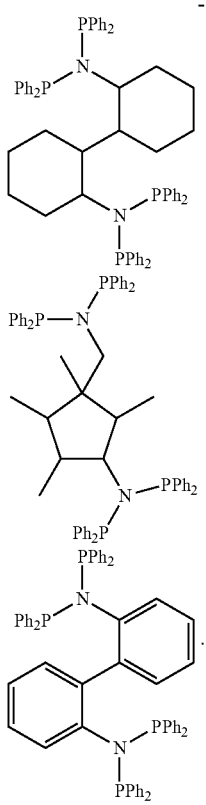

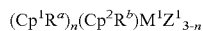

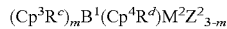

5. The catalyst composition of claim 1, wherein the metallocene compound includes one or more selected from compounds represented by the following Chemical Formulae 3 to 6:

$$(Cp^1R^a)_n(Cp^2R^b)M^1Z^1{}_{3-n} \quad \text{[Chemical Formula 3]}$$

wherein $M^1$ is a Group 4 transition metal;
$Cp^1$ and $Cp^2$ are the same as or different from each other, and each independently any one selected from the group consisting of cyclopentadienyl, indenyl, 4,5,6,7-tetrahydro-1-indenyl, and fluorenyl radicals, which may be substituted with hydrocarbon having 1 to 20 carbon atoms;
$R^a$ and $R^b$ are the same as or different from each other, and each independently hydrogen, C1 to C20 alkyl, C1 to C10 alkoxy, C2 to C20 alkoxyalkyl, C6 to C20 aryl, C6 to C10 aryloxy, C2 to C20 alkenyl, C7 to C40 alkylaryl, C7 to C40 arylalkyl, C8 to C40 arylalkenyl, or C2 to C10 alkynyl;
$Z^1$ is a halogen atom, C1 to C20 alkyl, C2 to C10 alkenyl, C7 to C40 alkylaryl, C7 to C40 arylalkyl, C6 to C20 aryl, substituted or unsubstituted C1 to C20 alkylidene, a substituted or unsubstituted amino group, C2 to C20 alkylalkoxy, or C7 to C40 arylalkoxy;
n is 1 or 0;

$$(Cp^3R^c)_mB^1(Cp^4R^d)M^2Z^2{}_{3-m} \quad \text{[Chemical Formula 4]}$$

wherein $M^2$ is a Group 4 transition metal;
$Cp^3$ and $Cp^4$ are the same as or different from each other, and each independently any one selected from the group consisting of cyclopentadienyl, indenyl, 4,5,6,7-tetrahydro-1-indenyl, and fluorenyl radicals, which may be substituted with hydrocarbon having 1 to 20 carbon atoms;

$R^c$ and $R^d$ are the same as or different from each other, and each independently hydrogen, C1 to C20 alkyl, C1 to C10 alkoxy, C2 to C20 alkoxyalkyl, C6 to C20 aryl, C6 to C10 aryloxy, C2 to C20 alkenyl, C7 to C40 alkylaryl, C7 to C40 arylalkyl, C8 to C40 arylalkenyl, or C2 to C10 alkynyl;
$Z^2$ is a halogen atom, C1 to C20 alkyl, C2 to C10 alkenyl, C7 to C40 alkylaryl, C7 to C40 arylalkyl, C6 to C20 aryl, substituted or unsubstituted C1 to C20 alkylidene, a substituted or unsubstituted amino group, C2 to C20 alkylalkoxy, or C7 to C40 arylalkoxy;
$B^1$ is one or more of carbon, germanium, silicon, phosphorus, or nitrogen-containing radical, or a combination thereof, which crosslinks a $Cp^3R^c$ ring with a $Cp^4R^d$ ring, or crosslinks one $Cp^4R^d$ ring to $M^2$;
m is 1 or 0;

$$(Cp^5R^e)B^2(J)M^3Z^3{}_2 \quad \text{[Chemical Formula 5]}$$

wherein $M^3$ is a Group 4 transition metal;
$Cp^5$ is any one selected from the group consisting of cyclopentadienyl, indenyl, 4,5,6,7-tetrahydro-1-indenyl, and fluorenyl radicals, which may be substituted with hydrocarbon having 1 to 20 carbon atoms;
$R^e$ is hydrogen, C1 to C20 alkyl, C1 to C10 alkoxy, C2 to C20 alkoxyalkyl, C6 to C20 aryl, C6 to C10 aryloxy, C2 to C20 alkenyl, C7 to C40 alkylaryl, C7 to C40 arylalkyl, C8 to C40 arylalkenyl, or C2 to C10 alkynyl;
$Z^3$ is a halogen atom, C1 to C20 alkyl, C2 to C10 alkenyl, C7 to C40 alkylaryl, C7 to C40 arylalkyl, C6 to C20 aryl, substituted or unsubstituted C1 to C20 alkylidene, a substituted or unsubstituted amino group, C2 to C20 alkylalkoxy, or C7 to C40 arylalkoxy;
$B^2$ is any one or more of carbon, germanium, silicon, phosphorus, or nitrogen-containing radical, or a combination thereof, which crosslinks a $Cp^5R^e$ ring with J; and
J is any one selected from the group consisting of $NR^f$, O, $PR^f$ and S, wherein $R^f$ is C1 to C20 alkyl, aryl, substituted alkyl, or substituted aryl;

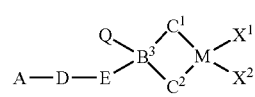

[Chemical Formula 6]

wherein A is hydrogen, halogen, a C1 to C20 alkyl group, a C2 to C20 alkenyl group, a C6 to C20 aryl group, a C7 to C20 alkylaryl group, a C7 to C20 arylalkyl group, a C1 to C20 alkoxy group, a C2 to C20 alkoxyalkyl group, a C3 to C20 heterocycloalkyl group, or a C5 to C20 heteroaryl group;
D is —O—, —S—, —N(R)- or —Si(R)(R')—, wherein R and R' are the same as or different from each other, and each independently hydrogen, halogen, a C1 to C20 alkyl group, a C2 to C20 alkenyl group, or a C6 to C20 aryl group;
E is a C1 to C10 linear or branched alkylene group;
$B^3$ is carbon, silicon, or germanium;
Q is hydrogen, halogen, a C1 to C20 alkyl group, a C2 to C20 alkenyl group, a C6 to C20 aryl group, a C7 to C20 alkylaryl group, or a C7 to C20 arylalkyl group;
M is a Group 4 transition metal;
$X^1$ and $X^2$ are the same as or different from each other, and each independently halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group;

$C^1$ and $C^2$ are the same as or different from each other, and each independently represented by any one of the following Chemical Formula 7a, Chemical Formula 7b, or Chemical Formula 7c, provided that both $C^1$ and $C^2$ are not Chemical Formula 7c;

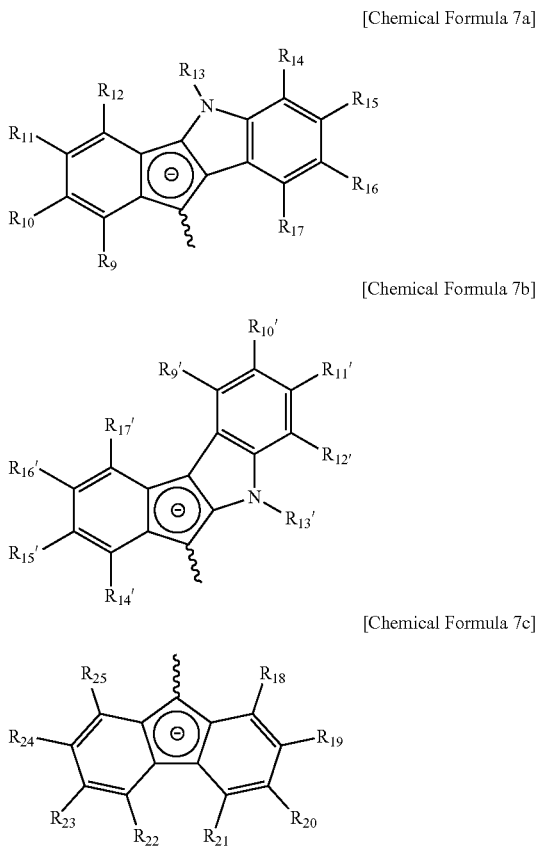

[Chemical Formula 7a]

[Chemical Formula 7b]

[Chemical Formula 7c]

wherein $R_9$ to $R_{25}$ and $R_9'$ to $R_{17}'$ are the same as or different from each other, and each independently hydrogen, halogen, a C1 to C20 alkyl group, a C2 to C20 alkenyl group, a C1 to C20 alkylsilyl group, a C1 to C20 silylalkyl group, a C1 to C20 alkoxysilyl group, a C1 to C20 alkoxy group, a C6 to C20 aryl group, a C7 to C20 alkylaryl group, or a C7 to C20 arylakyl group, and two or more neighboring groups of $R_{18}$ to $R_{25}$ may be connected to each other to form a substituted or unsubstituted aliphatic or aromatic ring.

6. The catalyst composition of claim 1, wherein the first and second supported catalysts further include each independently the same or different one or more cocatalysts of an aluminum-containing first cocatalyst of the following Chemical Formula 8 and a borate-based second cocatalyst of the following Chemical Formula 9:

—[Al(R$_{26}$)—O]$_k$—      [Chemical Formula 8]

wherein $R_{26}$ is the same as or different from each other, and each independently a halogen radical, a hydrocarbyl radical having 1 to 20 carbon atoms, or a hydrocarbyl radical having 1 to 20 carbon atoms, which is substituted with halogen, and k is an integer of 2 or more, $T^+[BG_4]^-$      [Chemical Formula 9]

wherein $T^+$ is a polyatomic ion having a valence of +1, B is boron in +3 oxidation state, and Gs are each independently selected from the group consisting of a hydride group, a dialkylamido group, a halide group, an alkoxide group, an aryloxide group, a hydrocarbyl group, a halocarbyl group, and a halo-substituted hydrocarbyl group, and G has 20 or less carbon atoms, provided that G is a halide group in one or less position.

7. The catalyst composition of claim 1, wherein the support is selected from the group consisting of silica, silica-alumina, and silica-magnesia.

8. A method of preparing a polyolefin, comprising the step of polymerizing olefinic monomers in the presence of the catalyst composition of claim 1.

9. The method of claim 8, wherein the olefinic monomer is ethylene.

10. The method of claim 8, wherein the step of polymerizing the olefinic monomers includes the step of obtaining ethylene oligomers by oligomerization of the olefinic monomers; and the step of obtaining the polyolefin by polymerization of the ethylene oligomers produced by the oligomerization and the olefinic monomers.

11. The method of claim 10, wherein the step of obtaining the ethylene oligomers and the step of obtaining the polyolefin are performed in the same reactor sequentially or simultaneously.

12. The method of claim 8, wherein the step of polymerizing olefinic monomers is performed at a temperature of 5° C. to 200° C.

13. The method of claim 8, wherein the step of polymerizing olefinic monomers is performed at a pressure of 1 bar to 300 bar.

* * * * *